(12) United States Patent
Tamaki et al.

(10) Patent No.: US 12,722,141 B2
(45) Date of Patent: Sep. 1, 2026

(54) PARTICULATE WATER-ABSORBING AGENT

(71) Applicant: NIPPON SHOKUBAI CO., LTD., Osaka (JP)

(72) Inventors: Mariko Tamaki, Himeji (JP); Keita Onishi, Himeji (JP); Yuika Tamura, Himeji (JP); Kazushi Torii, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 797 days.

(21) Appl. No.: 17/912,565

(22) PCT Filed: Mar. 31, 2021

(86) PCT No.: PCT/JP2021/014046
§ 371 (c)(1),
(2) Date: Sep. 19, 2022

(87) PCT Pub. No.: WO2021/201177
PCT Pub. Date: Oct. 7, 2021

(65) Prior Publication Data

US 2023/0144119 A1 May 11, 2023

(30) Foreign Application Priority Data

Mar. 31, 2020 (JP) ................................ 2020-064626

(51) Int. Cl.
*B01J 20/26* (2006.01)
*A61L 15/24* (2006.01)
(Continued)

(52) U.S. Cl.
CPC ............ *B01J 20/267* (2013.01); *A61L 15/24* (2013.01); *A61L 15/60* (2013.01); *B01J 20/103* (2013.01);
(Continued)

(58) Field of Classification Search
None
See application file for complete search history.

(56) References Cited

U.S. PATENT DOCUMENTS 5,981,070 A 11/1999 Ishizaki et al.
2005/0113252 A1 * 5/2005 Miyake .................. A61L 15/60 502/402

(Continued)

FOREIGN PATENT DOCUMENTS

CN 102875944 A 1/2013
EP 629411 A1 12/1994

(Continued)

OTHER PUBLICATIONS

Japanese Office Action dated May 12, 2023, which issued in the corresponding Japanese Patent Application No. 2022-512669, including English translation.

(Continued)

*Primary Examiner* — Joseph D Anthony
(74) *Attorney, Agent, or Firm* — Dickinson Wright PLLC

(57) ABSTRACT

[Problem] To provide a particulate water-absorbing agent that can significantly reduce re-wet even when pressure is applied to the particulate water-absorbing agent from the outside when the particulate water-absorbing agent is in a swollen state.
[Solution] A particulate water-absorbing agent comprising a surface-crosslinked polyacrylic acid (salt)-based water-absorbing resin as a main component and satisfying the following expression (1).

$$AAP(2.06\,kPa) + RCAP(2.06\,kPa) \geq 0.58 \times CRC + 55.6, \quad (1)$$

(Continued)

wherein AAP (2.06 kPa) represents absorption capacity (g/g) under a pressure of 2.06 kPa, RCAP (2.06 kPa) represents retention capacity against pressure after swelling (g/g), and CRC represents absorption capacity without pressure (g/g).

15 Claims, 2 Drawing Sheets

(51) Int. Cl.
*A61L 15/60* (2006.01)
*B01J 20/10* (2006.01)
*B01J 20/28* (2006.01)
*C08F 220/06* (2006.01)

(52) U.S. Cl.
CPC ....... *B01J 20/28016* (2013.01); *C08F 220/06* (2013.01); *C08F 2810/20* (2013.01)

(56) References Cited

U.S. PATENT DOCUMENTS

| | | | | |
|---|---|---|---|---|
| 2008/0032888 | A1 | 2/2008 | Nakamura et al. | |
| 2014/0197360 | A1* | 7/2014 | Kitano | A61L 15/60 252/194 |
| 2015/0129799 | A1 | 5/2015 | Kobayashi et al. | |
| 2016/0235882 | A1 | 8/2016 | Noh et al. | |
| 2018/0001300 | A1* | 1/2018 | Nakatsuru | B01J 20/267 |
| 2018/0071714 | A1* | 3/2018 | Torii | B01J 20/261 |
| 2018/0298132 | A1 | 10/2018 | Yorino et al. | |
| 2018/0318792 | A1 | 11/2018 | Miyajima et al. | |
| 2019/0111411 | A1 | 4/2019 | Torii et al. | |
| 2019/0125921 | A1* | 5/2019 | Kimura | B01J 20/26 |

FOREIGN PATENT DOCUMENTS

| | | | |
|---|---|---|---|
| EP | 3318324 | A1 | 9/2018 |
| EP | 3711722 | A1 | 9/2020 |
| JP | H07-88171 | A | 4/1995 |
| JP | 2015-213911 | A | 12/2015 |
| JP | 2017-509757 | A | 4/2017 |
| WO | WO1997/003114 | A | 1/1997 |
| WO | WO2016/204302 | A1 | 12/2016 |
| WO | WO2017/057709 | A1 | 4/2017 |
| WO | WO2017/170605 | A1 | 10/2017 |

OTHER PUBLICATIONS

Indonesian Substantive Examination Result Phase I dated Jun. 27, 2023, which issued in the corresponding Indonesian Patent Application No. P00202210129, including English translation.

Chinese Office Action dated Mar. 29, 2024, which issued in the corresponding Chinese Patent Application No. 202180026001.1, including English translation.

European Search Report dated Aug. 25, 2023, which issued in the corresponding European Patent Application No. 21780477.2.

Indian Examination Report dated Nov. 24, 2022, which issued in the corresponding Indian Patent Application No. 202247055230, including English translation.

Indian Hearing Notice dated Dec. 21, 2023, which issued in the corresponding Indian Patent Application No. 202247055230, including English translation.

International Search Report and Written Opinion dated Jun. 1, 2021, which issued in the corresponding Japanese Patent Application No. PCT/JP2021/014046.

Chinese Office Action dated Jan. 22, 2025, which issued in the corresponding Chinese Patent Application No. 202180026001.1.

* cited by examiner

PARTICULATE WATER-ABSORBING AGENT

TECHNICAL FIELD

The present invention relates to a particulate water-absorbing agent having less re-wet under pressure even after liquid absorption.

BACKGROUND ART

A water-absorbing resin (SAP/Super Absorbent Polymer) is a water swellable, water insoluble polymer gelling agent. A particulate water-absorbing agent including a water-absorbing resin as a main component is used for absorbent articles in various applications such as a hygiene article such as disposable diapers, a sanitary napkin, or an incontinence product for an adult, a soil water retention agent for agriculture or horticulture, and a water blocking agent for industrial use. Many monomers and hydrophilic polymers have been proposed as raw materials for such a water-absorbing resin, and from the viewpoint of performance and cost, a polyacrylic acid (salt)-based water-absorbing resin using acrylic acid and/or a salt thereof as a monomer is most often used.

With the increase in performance of disposable diapers, which are the main use of the particulate water-absorbing agent, the particulate water-absorbing agent is required to have many functions (physical properties). Specific examples of the physical properties of the particulate water-absorbing agent are not limited to mere high fluid retention capacity, and include gel strength, a water soluble component, water absorption speed, absorption capacity under pressure, liquid permeability, particle size distribution, urine resistance, an antibacterial property, impact resistance (damage resistance), powder fluidity, a deodorizing property, coloration resistance (whiteness), and low dustiness. Among these, there is the physical property of so-called "wet-back" in which the liquid is re-released from the particulate water-absorbing agent in the direction of introduction of the liquid absorbed. The user feels uncomfortable with the liquid that comes into contact with the skin, and thus reducing the wet-back is a very important problem in the field of the water-absorbing resin (for example, Patent Literature 1).

As another related prior art, there is Patent Literature 2.

CITATION LIST

Patent Literature

[Patent Literature 1] Japanese Patent Laid-Open No. 2015-213911

[Patent Literature 2] International Publication No. WO 97/003114

SUMMARY OF INVENTION

Every time a liquid such as urine is discharged to an absorbent article such as disposable diapers, the absorbent article is not replaced, and usually the liquid is discharged to the absorbent article a plurality of times. The particulate water-absorbing agent that has absorbed the liquid is in a swollen state. Therefore, the user may use an absorbent article having a particulate water-absorbing agent in a swollen state. As described above, when the particulate water-absorbing agent is in a swollen state, in a daily movement, particularly even in a situation in which pressure is applied from the outside such as a state in which the body weight is applied (for example, a movement such as lying face up or sitting), it is necessary to improve the liquid retention capacity of the absorbent body and reduce the re-wet, and this can reduce a problem such as skin rash and allow the user to comfortably use the absorbent article for a long time. Conventionally, attention has been focused only on "how to absorb a liquid under a condition of load application," which is generally expressed by absorption capacity under pressure (AAP), but in a swollen state after liquid absorption, no attention has been paid to how much liquid can be retained even when a load is applied, and it is considered that there is room for improvement.

Therefore, an object of the present invention is to provide a particulate water-absorbing agent that can significantly reduce re-wet even when pressure is applied to the particulate water-absorbing agent from the outside when the particulate water-absorbing agent is in a swollen state.

The above problem is solved by a particulate water-absorbing agent including a surface-crosslinked polyacrylic acid (salt)-based water-absorbing resin as a main component and satisfying the following expression (1).

$$AAP(2.06\,kPa) + RCAP(2.06\,kPa) \geq 0.58 \times CRC + 55.6 \quad (1)$$

wherein AAP (2.06 kPa) represents absorption capacity (g/g) under a pressure of 2.06 kPa, RCAP (2.06 kPa) represents retention capacity against pressure after swelling (g/g), and CRC represents absorption capacity without pressure (g/g).

DESCRIPTION OF EMBODIMENTS

Figure 1:
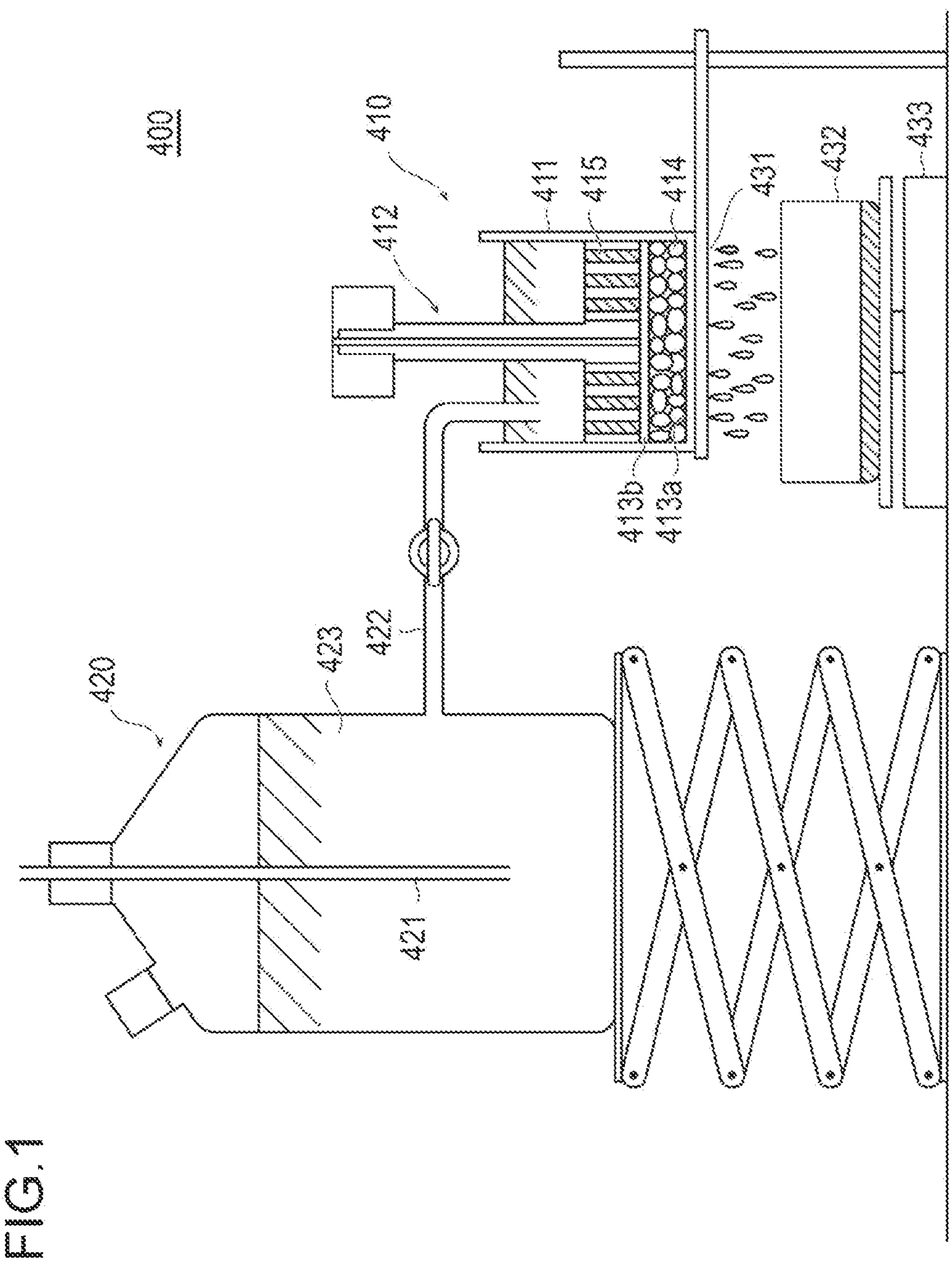
FIG. 1 is a schematic diagram showing an apparatus for measuring a gel permeation rate (GPR).

Hereinafter, the present invention will be described while showing the best embodiments. Throughout the specification, it should be understood that a singular expression also encompasses the concept thereof in the plural form, unless otherwise noted. Therefore, it should be understood that a singular article (for example, "a," "an," "the," or the like in the case of English) also encompasses the concept thereof in the plural form, unless otherwise noted. In addition, it should be understood that a term used herein is used in a meaning that is commonly used therefor in the art, unless otherwise noted. Therefore, unless otherwise defined, all technical and scientific terms that are used herein have the same meanings as those generally understood by those skilled in the art to which the present invention pertains. In case of contradiction, the present specification (including a definition) prevails. The present invention is not limited to the following embodiments, and various modifications can be made within the scope of the claims.

[1] Definitions of Terms (1-1) "Water-Absorbing Resin"

The "water-absorbing resin" in the present invention refers to a water swellable, water insoluble polymer crosslinked body, and refers to a resin that satisfies the following physical properties. That is, the "water-absorbing resin" refers to a polymer crosslinked body that satisfies the physical properties of a CRC specified by ERT 441.2-02 of 5 g/g or more for "water swellable" and an Ext specified by ERT 470.2-02 of 50% by weight or less for "water insoluble."

The above water-absorbing resin can be appropriately designed according to the intended use, is not particularly limited, and is preferably a hydrophilic crosslinked polymer obtained by crosslinking and polymerizing an unsaturated monomer having a carboxyl group. In addition, the water-absorbing resin is not limited to a formation in which a polymer accounts for the total amount (100% by weight), and may also be a water-absorbing resin composition including an additive or the like as long as the above physical properties (CRC and Ext) are satisfied.

Further, the water-absorbing resin in the present invention is not limited to the final product and may refer to an intermediate in the production step of the water-absorbing resin (for example, a crosslinked hydrogel polymer after polymerization, a dry polymer after drying, or a water-absorbing resin powder before surface crosslinking); and all of these are collectively referred to as a "water-absorbing resin." Examples of the form of the water-absorbing resin includes a sheet form, a fibrous form, a film form, a particulate form, and a gel form, and the water-absorbing resin of the present invention is mainly in a particulate form (powder).

(1-2) "Particulate Water-Absorbing Agent"

Herein, the water-absorbing agent includes a water-absorbing resin as a main component. As used herein, the particulate water-absorbing agent means a water-absorbing agent (including a water-absorbing resin particle as a main component) in a particulate form (also referred to as a powder form), and this is referred to as a particulate water-absorbing agent, regardless of whether this is a single particle of a particulate water-absorbing agent or a plurality of particles of a particulate water-absorbing agent. "Particulate" means having the form of a particle, which refers to a solid or liquid granular small object having a measurable size (Glossary of Technical Terms in Japanese Industrial Standards, 4th Edition, p. 2002). Herein, the particulate water-absorbing agent may be simply referred to as a water-absorbing agent.

A water-based liquid is not limited to water, and may be urine, blood, sweat, feces, waste liquid, moisture, vapor, ice, a mixture of water and an organic solvent and/or an inorganic solvent, rainwater, groundwater, or the like, and is not particularly limited as long as it includes water. Preferable examples thereof include urine, menstrual blood, sweat, and another body fluid.

The particulate water-absorbing agent according to the present invention is suitably used as a hygienic material for absorbing a water-based liquid. The particulate water-absorbing agent of the present invention includes, as a main component, a surface-crosslinked polyacrylic acid (salt)-based water-absorbing resin (particle) (hereinafter, also simply referred to as a polyacrylic acid (salt)-based water-absorbing resin). That is, the surface-crosslinked polyacrylic acid (salt)-based water-absorbing resin is included preferably in an amount of 60 to 100% by weight, 70 to 100% by weight, 80 to 100% by weight, or 90 to 100% by weight in the particulate water-absorbing agent. Additionally, the particulate water-absorbing agent optionally includes another water-absorbing resin particle, water, and/or an additive such as a water insoluble inorganic particle or a water-soluble polyvalent metal cation-containing compound. A suitable moisture content of the particulate water-absorbing agent is 0.2 to 30% by weight. That is, a water-absorbing resin composition in which these components are integrated is also encompassed in the scope of the particulate water-absorbing agent.

The upper limit of the polyacrylic acid (salt)-based water-absorbing resin in the water-absorbing agent is about 99% by weight, further about 97% by weight, and particularly about 95% by weight, and the water-absorbing agent further includes preferably water or an additive (a water insoluble inorganic particle or a water soluble polyvalent metal cation-containing compound) described later.

In addition, the particulate water-absorbing agent of the present invention contains a polyacrylic acid (salt)-based water-absorbing resin as a main component, and the particulate water-absorbing agent may contain another water-absorbing resin. Examples of the another water-absorbing resin include a polysulfonic acid (salt)-based water-absorbing resin, a maleic anhydride (salt)-based water-absorbing resin, a polyacrylamide-based water-absorbing resin, a polyvinyl alcohol-based water-absorbing resin, a polyethylene oxide-based water-absorbing resin, a polyaspartic acid (salt)-based water-absorbing resin, a polyglutamic acid (salt)-based water-absorbing resin, a polyarginic acid (salt)-based water-absorbing resin, a starch-based water-absorbing resin, and a cellulose-based resin.

(1-3) "Polyacrylic Acid (Salt)" and "Polyacrylic Acid (Salt)-Based Water-Absorbing Resin"

The "polyacrylic acid (salt)" in the present invention refers to a polyacrylic acid and/or a salt thereof. In addition, the polyacrylic acid (salt)-based water-absorbing resin includes acrylic acid and/or a salt thereof (hereinafter, referred to as "acrylic acid (salt)") as a repeating unit as a main component, and is preferably obtained by surface crosslinking of polyacrylic acid (salt) internally crosslinked by a graft component.

The polyacrylic acid (salt)-based water-absorbing resin is preferably in a particulate form (also referred to as a powder form) in the particulate water-absorbing agent.

The above "main component" means that the amount (content) of the acrylic acid (salt) used is usually 50 to 100 mol %, preferably 70 to 100 mol %, more preferably 90 to 100 mol %, and further preferably substantially 100 mol % based on the total amount of the monomers (excluding an internal crosslinking agent) used for polymerization.

(1-4) "EDANA" and "ERT"

"EDANA" is an abbreviation for the European Disposables and Nonwovens Associations, and "ERT" is an abbreviation for European standard (substantially world standard) methods for measuring water-absorbing resin (EDANA Recommended Test Methods). In the present invention, unless otherwise specified, a physical property of the water-absorbing resin is measured according to the original ERT (revised in 2002/known literature).

(1-5) "PSD" (ERT 420.2-02)

"PSD" is an abbreviation for Particle Size Distribution, and means a particle size distribution of a particulate water-absorbing agent or a water-absorbing resin measured by sieve classification.

The weight average particle diameter (D50) and the logarithmic standard deviation ($\sigma\zeta$) of a particle size distribution are measured by the same methods as described in "(3) Mass-Average Particle Diameter (D50) and Logarithmic Standard Deviation (σζ) of Particle Diameter Distribution" described in U.S. Pat. No. 7,638,570.

(1-6) Others

As used herein, "X to Y" representing a range means "X or more and Y or less." In addition, unless otherwise noted, "t (ton)", which is a unit of weight, means "Metric ton," and "ppm" means "ppm by weight" or "ppm by mass." Further, "weight" and "mass," "parts by weight" and "parts by mass," and "% by weight" and "% by mass" are each treated as synonyms. In addition, " . . . acid (salt)" means " . . . acid and/or a salt thereof," and "(meth)acrylic" means "acrylic and/or methacrylic."

In addition, "liter" may be denoted as "l" or "L", and "% by weight" may be denoted as "wt %" for convenience. Further, when measuring a trace component, below the detection limit is notated as N.D (Non Detected).

[2] Particulate Water-Absorbing Agent

The particulate water-absorbing agent of the present invention is a particulate water-absorbing agent including a polyacrylic acid (salt)-based water-absorbing resin prepared by surface crosslinking as a main component and satisfying the expression (1).

The particulate water-absorbing agent of the present invention can significantly reduce re-wet even if pressure is applied to the particulate water-absorbing agent from the outside when the particulate water-absorbing agent is in a swollen state.

Hereinafter, the value determined by AAP (2.06 kPa)+RCAP (2.06 kPa) is also referred to as a value (A), and the value determined by 0.58×CRC+55.6 is also referred to as a value (B).

When the particulate water-absorbing agent does not satisfy the expression (1), that is, the value (A)<the value (B), the Re-Wet becomes remarkably large after the particulate water-absorbing agent absorbs water and swells.

The value (A) is the sum of AAP (2.06 kPa) and RCAP (2.06 kPa). "AAP" is an abbreviation for Absorption Against Pressure, and means the absorption capacity under pressure of a particulate water-absorbing agent. "RCAP" is an abbreviation for Retention Capacity Against Pressure, and means the absorption capacity under pressure of a particulate water-absorbing agent when the particulate water-absorbing agent swells. In addition, "CRC" is an abbreviation for Centrifuge Retention Capacity, and means the absorption capacity without pressure (sometimes referred to as "fluid retention capacity") of a particulate water-absorbing agent or a water-absorbing resin. Usually, the fluid retention capacity decreases under pressure, and thus in the same particulate water-absorbing agent, AAP (2.06 kPa) [g/g] <CRC (2.06 kPa) [g/g].

When assuming actual use of a water absorbent article, various cases of situations of use are assumed, such as a case where urination occurs in a state in which the body weight is applied and a case where the article swells without pressure during urination but is pressurized with a movement. In the process of solving the problem of "reducing the Re-Wet after the particulate water-absorbing agent absorbs water and swells," the present inventors have found that the "liquid retention capacity" (the absorption amount that the amount of the liquid retained in the gaps between water-absorbing resin particles (including the primary particles and/or the secondary particles in which the primary particles aggregate) is added to the fluid retention capacity of water-absorbing resin particles themselves (that is, CRC)) in various cases is important, and focused on AAP (2.06 kPa) and RCAP (2.06 kPa) from among a large number of physical properties of a particulate water-absorbing agent.

Here, in the problem of the present application of "significantly reducing re-wet even if pressure is applied to the particulate water-absorbing agent from the outside when the particulate water-absorbing agent is in a swollen state," it is also considered that if RCAP is high, the object is solved. However, it has become clear in the process of a study by the present inventors that the re-wet in a swollen state is not sufficient only by considering RCAP, which is the absorption capacity under pressure at the time of swelling. For example, this fact is understood because although the RCAP of Comparative Example 1-5 described later is higher than that of Example 1-8, the liquid return of the particulate water-absorbing agent at the time of swelling is significantly reduced. Then, the present inventors have found that the total sum of AAP (2.06 kPa)+RCAP (2.06 kPa) and CRC are important factors for the re-wet of the particulate water-absorbing agent at the time of swelling, and further found that a novel particulate water-absorbing agent satisfying the expression (1) significantly suppresses the re-wet of the particulate water-absorbing agent at the time of swelling.

It should be noted that "wet-back" (sometimes referred to as Re-Wet), which is usually used as evaluation of a physical property of a water-absorbing resin, is an evaluation using an absorbent sheet (absorbent body) in which an absorbent layer including a water-absorbing resin (water-absorbing agent), pulp, and the like is stacked with a non-woven fabric or the like, not an evaluation of the water-absorbing resin (water-absorbing agent) itself. In addition, in the above Re-Wet evaluation, it cannot be deemed that the water-absorbing resin included in the absorbent body is in a saturated state (it evaluates re-wet under load after absorbing the liquid on the surface of the absorbent body a plurality of times at intervals of 30 minutes), and the Re-Wet evaluation does not evaluate the liquid retention capacity in a state in which the particulate water-absorbing agent in a "swollen state" is further pressurized, which is the problem of the present application.

In addition, the particulate water-absorbing agent more preferably satisfies the following expression (2).

$$AAP(2.06\,kPa) + RCAP(2.06\,kPa) \geq 0.58 \times CRC + 56.0 \quad (2)$$

A particulate water-absorbing agent satisfying the above expression (2) is excellent in liquid retention capacity when the swollen absorbent body is pressurized.

In particular, when the CRC of a particulate water-absorbing agent is less than 37.0 g/g, the particulate water-absorbing agent more preferably satisfies the above expression (2).

Further, the particulate water-absorbing agent more preferably satisfies the following expression (3).

$$AAP(2.06\,kPa) + RCAP(2.06\,kPa) \geq 0.58 \times CRC + 56.5 \quad (3)$$

A particulate water-absorbing agent satisfying the above expression (3) is excellent in liquid retention capacity when the swollen absorbent body is pressurized.

In particular, when the CRC of a particulate water-absorbing agent is less than 37.0 g/g, the particulate water-absorbing agent more preferably satisfies the above expression (3).

The value (A) is not particularly limited, and is preferably larger than 76.0 g/g. That is, the particulate water-absorbing agent preferably satisfies the following expression (A).

$$AAP(2.06\ kPa) + RCAP(2.06\ kPa) > 76.0 \tag{A}$$

When the value (A) is larger than 76.0 g/g, the reduction of liquid return after the swelling of the particulate water-absorbing agent is more likely to be exhibited. The upper limit of the value (A) is not particularly limited, and is usually 90.0 g/g or less, and may be 85.0 g/g or less.

In the calculation of the expressions (1) to (3) and the expression (A), measured values to the first decimal place of AAP (2.06 kPa), RCAP (2.06 kPa), and CRC are used, and in the calculation of the value (A), the value (B), and the right-hand side of each of the expressions (2) and (3), the second decimal place of the values calculated using the above measured values is rounded off to use the values to the first decimal place.

(2-1) CRC (Centrifuge Retention Capacity) (ERT 441.2-02)

"CRC" is an abbreviation for Centrifuge Retention Capacity, and means the absorption capacity without pressure of a particulate water-absorbing agent or a water-absorbing resin (sometimes referred to as "fluid retention capacity").

Specifically, CRC refers to the fluid retention capacity (unit; g/g) after 0.2 g of a particulate water-absorbing agent or a water-absorbing resin is placed in a non-woven fabric bag, then the bag is immersed in a large excess of a 0.9% by weight sodium chloride aqueous solution for 30 minutes to cause free swelling followed by draining using a centrifuge (250 G).

The CRC (centrifuge retention capacity) of the particulate water-absorbing agent of the present invention is preferably 30 g/g or more, more preferably 31 g/g or more, further preferably 32 g/g or more, and further more preferably 33 g/g or more. When the CRC is 30 g/g or more, the absorption capacity becomes appropriate, and the performance as an absorbent body of a hygiene article such as disposable diapers is ensured. In addition, the CRC (centrifuge retention capacity) of the particulate water-absorbing agent is preferably 70 g/g or less, more preferably 60 g/g or less, further more preferably 50 g/g or less, and particularly preferably 40 g/g or less. When the CRC is 70 g/g or less, the speed of absorbing, for example, a body fluid such as urine or blood is retained, and thus the particulate water-absorbing agent of the present invention is also suitable for use in high water absorption speed type disposable diapers or the like. The CRC can be controlled by the type or the amount of the internal crosslinking agent or the like.

(2-2) Absorption Capacity Under Pressure (AAP) (ERT 442.2-02)

"AAP" is an abbreviation for Absorption Against Pressure, and means the absorption capacity under pressure of a particulate water-absorbing agent or a water-absorbing resin.

Specifically, AAP (2.06 kPa) refers to the fluid retention capacity (unit; g/g) after 0.9 g of a particulate water-absorbing agent or a water-absorbing resin is swollen in a large excess of a 0.9% by weight sodium chloride aqueous solution for 1 hour under a load of 2.06 kPa (21 g/cm$^2$, 0.3 psi). The load condition may be changed to 4.83 kPa (49 g/cm$^2$, 0.7 psi) for measurement. The AAP in this case is denoted as AAP (4.83 kPa).

In addition, ERT 442.2-02 uses the term Absorption Under Pressure, but this term is substantially the same.

The AAP (2.06 kPa) of the particulate water-absorbing agent of the present invention is preferably 20 g/g or more, more preferably 24 g/g or more, further preferably 26 g/g or more, further more preferably 28 g/g or more, particularly preferably 29 g/g or more, and most preferably 30 g/g or more. The upper limit is not particularly limited, and is preferably 40 g/g or less. By satisfying the above conditions, the AAP (2.06 kPa) is high to some extent, and thereby the condition of the expression (1) can be easily satisfied. In addition, disposable diapers produced using the particulate water-absorbing agent have an excellent ability to absorb urine from pulp, can reduce the Re-Wet, and can suppress skin rash and urine leakage. As will be understood by referring to the Examples and Comparative Examples described later, there is no correlation between the high AAP (2.06 kPa) and the satisfaction of the expression (1).

In addition, the AAP (4.83 kPa) of the particulate water-absorbing agent of the present invention is preferably 10 g/g or more, more preferably 13 g/g or more, further preferably 17 g/g or more, and particularly preferably 20 g/g or more. The upper limit is not particularly limited, and is preferably 30 g/g or less. By satisfying the above conditions, disposable diapers produced using the above particulate water-absorbing agent have an excellent ability to absorb urine from pulp, can reduce the Re-Wet, and can suppress skin rash and urine leakage. The AAP can be controlled by the type or the amount of a surface crosslinking agent or the like.

(2-3) Retention Capacity Against Pressure (RCAP)

"RCAP" is an abbreviation for Retention Capacity Against Pressure, and means the absorption capacity under pressure of a particulate water-absorbing agent when the particulate water-absorbing agent swells.

An RCAP test can be measured using the cylinder, piston, and weight used in the Gel Bed Permeability Test described in U.S. Pat. No. 8,269,060. Specifically, the apparatus illustrated in FIG. 1 of U.S. Pat. No. 8,269,060 is used.

Before carrying out the test, the total weight of the cylinder, the piston, and the weight is measured, and the value thereof is taken as Wa [g]. About 0.9 g of a sample to be tested is weighed out and uniformly scattered on the bottom surface of the cylinder, and the cylinder is immersed in a test solution (0.9% by weight sodium chloride aqueous solution) for 60 minutes to swell the sample free of any restraining load. After 60 minutes, the piston and the weight (total weight of about 596 g) are placed on the sample in the cylinder, and the cylinder is pulled up from the test solution, placed on a JIS standard sieve having an opening of 2000 m, and drained for about 1 minute. After draining, the water droplet adhering to the lower part of the cylinder is removed using Kimwipes (S-200 manufactured by Nippon Paper Crecia Co., Ltd.) or the like, the weight is measured, and the obtained value is taken as Wb [g]. The removal of the water droplet adhering to the lower part of the cylinder using Kimwipes is intended to remove the water adhering to the outside of the cylinder so as not to remove the water included in the swollen gel layer in the cylinder, and is carried out by wiping within 0.5 seconds in such a way that no pressure by Kimwipes is applied. RCAP is calculated by the following expression (4).

[Expression 1]

$$RCAP[g/g] = \frac{Wo[g] - Wa[g]}{\text{Weight [g] of sample}} \quad (4)$$

The RCAP (2.06 kPa) of the particulate water-absorbing agent of the present invention is preferably 18 g/g or more, more preferably 24 g/g or more, further more preferably 30 g/g or more, particularly preferably 40 g/g or more, and most preferably 43 g/g or more. The upper limit is not particularly limited, and is preferably 60 g/g or less. By satisfying the above conditions, the RCAP (2.06 kPa) is high to some extent, and thereby the condition of the expression (1) can be easily satisfied. In addition, disposable diapers produced using the particulate water-absorbing agent has an excellent ability to absorb urine from pulp, can reduce the Re-Wet, and can suppress skin rash and urine leakage. As will be understood by referring to the Examples and Comparative Examples described later, there is no correlation between the high RCAP (2.06 kPa) and the satisfaction of the expression (1).

The value of RCAP (2.06 kPa) can be controlled by controlling the method for producing the water-absorbing resin, for example, the mixing time of an additive (for example, a water insoluble inorganic particle) or the content of a soluble component.

(2-3) Gel Permeation Rate (GPR)

As used herein, the "liquid permeability" of a particulate water-absorbing agent refers to the flowability of a liquid that passes between swollen gel particles under load. As an index of this, gel permeation rate (GPR) is used. Measurement of the GPR of the particulate water-absorbing agent is carried out by referring to the Saline Flow Conductivity (SFC) test described in U.S. Pat. No. 5,849,405, changing the measurement conditions, and following the procedure below.

As an apparatus for measurement, an apparatus 400 illustrated in FIG. 1 is used. The apparatus 400 is roughly composed of a container 410 and a tank 420. The container 410 is provided with a cell 411 (inner diameter of 6 cm), a swollen gel 414 (which has absorbed a particulate water-absorbing agent) is accommodated inside the cell 411, and a liquid 423 can be introduced inside the same. In addition, by fitting the piston 412 into the cell 411, pressure can be applied to the swollen gel 414. Wire meshes 413*a* and 413*b* (No. 400 stainless steel wire meshes, opening of 38 am) are placed on the bottom surface of the cell 411 and the bottom surface of the piston 412 so that the swollen gel 414 (and the particulate water-absorbing agent) cannot pass through the bottom surfaces. Here, as the liquid 423, a 0.90% by mass sodium chloride aqueous solution is used. The tank 420 stores the liquid 423 inside. The liquid 423 is introduced into the cell 411 through an L-shaped tube 422 with a cock. In addition, a glass tube 421 is inserted into the tank 420, and the inside of the glass tube 421 is filled with air. Thereby, the height of the lower end of the glass tube 421 and the liquid level in the cell 411 can be made the same. That is, while the liquid level of the liquid 423 in the tank 420 is above the lower end of the glass tube 421, the liquid level in the cell 411 can be kept constant. In this measurement, the height difference between the lower liquid level of the liquid 423 in the tank 420 (that is, the lower end of the glass tube 421) and the bottom surface of the swollen gel 414 is set to 4 cm. That is, according to the apparatus 400, the liquid 423 having a constant hydrostatic pressure can be introduced into the cell 411. A hole 415 is formed in the piston 412, and thus the liquid 423 flows through the hole 415, and further flows through the swollen gel 414 layer, and flows out of the cell 411. The container 410 is mounted on a stainless steel wire mesh 431 that does not block the passage of the liquid 423. Because of this, the liquid 423 flowing out of the cell 411 is finally collected in a collection container 432. Then, the amount of the liquid 423 collected in the collection container 432 can be weighed using an even balance 433.

The specific method for measuring the gel permeation rate (GPR) is as follows. The following operations are carried out at room temperature (20 to 25° C.).

(1) A particulate water-absorbing agent (0.900 g) is uniformly placed in the cell 411.

(2) The particulate water-absorbing agent is allowed to absorb the liquid (0.90% by mass sodium chloride aqueous solution) for 60 minutes under no pressure to form the swollen gel 414.

(3) A piston is placed on the swollen gel 414 to bring the gel into a pressurized state at 0.3 psi (2.06 kPa).

(4) The liquid 423 is introduced into the cell 411 and allowed to pass through the swollen gel 414 layer, while keeping the hydrostatic pressure at a constant value of 3923 dynes/cm$^2$.

(5) The amount of the liquid 423 that passes through the swollen gel 414 layer is recorded at intervals of 5 seconds for 3 minutes. That is, the flow speed of the liquid 423 passing through the swollen gel 414 layer is measured. The even balance 433 and a computer (not shown) are used for the measurement.

(6) The gel permeation rate (GPR) [g/min] is calculated by averaging the flow speeds 1 to 3 minutes after the start of the passage of the liquid 423.

The gel permeation rate (GPR) of the particulate water-absorbing agent of the present invention is preferably 20 g/min or more. When the gel permeation rate (GPR) is 20 g/min or more, the liquid diffusibility when the particulate water-absorbing agent is used for an absorbent body is excellent. The gel permeation rate (GPR) of the particulate water-absorbing agent is more preferably 22 g/min or more, further preferably 24 g/min or more, and particularly preferably 26 g/min or more. The upper limit is not particularly limited, and is preferably 300 g/min or less, and more preferably 150 g/min or less.

The value of the gel permeation rate (GPR) can be controlled by controlling, for example, the amount of the internal crosslinking agent of the water-absorbing resin, the amount of the surface crosslinking agent, the time of the surface crosslinking reaction, or the like.

(2-4) Blocking Ratio after Moisture Absorption

The "fluidity after moisture absorption" in the present invention is an evaluation of blocking, caking, or fluidity as a powder when a particulate water-absorbing agent is left for 1 hour under conditions of a temperature of 25° C. and a relative humidity of 90% RH, and is determined by blocking ratio after moisture absorption. The method for calculating the blocking ratio after moisture absorption will be described in detail in Examples. Briefly, a particulate water-absorbing agent is placed on a sieve and classified, the weight of the particulate water-absorbing agent remaining on the sieve (W1 [g]) and the weight of the particulate water-absorbing agent that has passed through the sieve (W2 [g]) are measured, and the fluidity after moisture absorption is calculated according to the following expression.

$$\text{Blocking ratio after moisture absorption [\% by weight]} = \{W1/(W1+W2)\} \times 100.$$

The details of the measurement method are as described in Examples.

The blocking ratio after moisture absorption of the particulate water-absorbing agent of the present invention is usually 50% by weight or less, preferably 40% by weight or less, more preferably 30% by weight or less, further preferably 20% by weight or less, more further preferably 10% by weight or less, and most preferably 0% by weight. The blocking ratio after moisture absorption of the particulate water-absorbing agent of the present invention can be 0 to 50% by weight, 0 to 40% by weight, 0 to 30% by weight, 0 to 20% by weight, or 0 to 10% by weight. When the blocking ratio after moisture absorption is 40% by weight or less, the particulate water-absorbing agent is easy to handle even in a humid environment, and, for example when producing a thin absorbent body for a hygienic material, the problem of the occurrence of aggregation and clogging in a transfer pipe of a production plant or the inability to mix uniformly with a hydrophilic fiber is less likely to occur. Therefore, by satisfying the above conditions, when an absorbent body is prepared using the particulate water-absorbing agent and a fiber base material, the adhesion thereof to the apparatus and equipment can be reduced.

The blocking ratio after moisture absorption can be controlled by the type of the agent added to improve the fluidity at the time of moisture absorption or the amount thereof added.

(2-5) Flow Rate (ERT 450.2-02)

The flow rate means the powder fluidity of a particulate water-absorbing agent.

Specifically, 100 g of a particulate water-absorbing agent is put into a funnel equipped with a damper at the bottom thereof, the damper is opened, the time from the start of the flow to the end of the flow is measured to calculate the amount of the particulate water-absorbing agent flowing per unit time, and this is taken as the flow rate.

The flow rate of the particulate water-absorbing agent of the present invention is preferably 8.5 g/s or more. When the flow rate is less than 8.5 g/s, the fluidity of the particulate water-absorbing agent is low, and thus the following problems may occur: it is difficult to supply the particulate water-absorbing agent to a hopper or transport the particulate water-absorbing agent using a feeder, and the particulate water-absorbing agent cannot be mixed uniformly with a hydrophilic fiber when producing an absorbent body for a hygienic material.

(2-6) Amount of Dust

The amount of dust of the particulate water-absorbing agent of the present invention is preferably 400 mg/kg or less per water-absorbing agent. When the amount of dust of the water-absorbing agent is equal to or less than the above upper limit, the dust is sufficiently reduced and the handleability of the water-absorbing agent is excellent. The amount of dust of the water-absorbing agent is more preferably 300 mg/kg or less, further preferably 250 mg/kg or less, and particularly preferably 200 mg/kg or less per water-absorbing agent. The ideal value is 0 mg/kg water-absorbing agent, but the lower limit is usually 10 mg/kg or more and may be 15 mg/kg or more or 20 mg/kg or more per water-absorbing agent, in practical use and in consideration of productivity on an industrial scale.

The amount of dust of the particulate water-absorbing agent is calculated by the method described in Examples.

(2-7) Surface Tension

Surface tension refers to the work (free energy) required to increase the surface area of a solid or a liquid, expressed per unit area. The surface tension referred to in the present application refers to the surface tension of an aqueous solution obtained by dispersing a particulate water-absorbing agent in a 0.90% by mass sodium chloride aqueous solution. The surface tension of a water-absorbing agent is measured by the following procedure. That is, 50 ml of physiological saline adjusted to 20° C. is placed in a 100 ml beaker sufficiently washed, and the surface tension of the physiological saline is first measured using a tensiometer (K11 automatic tensiometer manufactured by KRUSS GmbH). Next, in the beaker including the physiological saline adjusted to 20° C. after measuring the surface tension, a 25 mm long fluororesin rotor sufficiently washed and 0.5 g of a particulate water-absorbing agent are placed and stirred for 4 minutes under a condition of 500 rpm. After 4 minutes, the stirring is stopped, and after the water-containing particulate water-absorbing agent has settled, the surface tension of the supernatant liquid is measured by carrying out the same operation again. In the present invention, a plate method using a platinum plate is adopted, and before each measurement, the plate is sufficiently washed with deionized water and heated and cleaned using a gas burner before use.

The surface tension of the particulate water-absorbing agent of the present invention is preferably 65 [mN/m] or more, and in more preferable order, 66 [mN/m] or more, 68 [mN/m] or more, 70 [mN/m] or more, 71 [mN/m] or more, or 72 [mN/m] or more. When the surface tension satisfies the above conditions, the Re-Wet in disposable diapers can be reduced more. The upper limit is usually 75 [mN/m], which is sufficient.

(2-8) Particle Form

The water-absorbing resin (powder) is preferably in an irregularly crushed form as a particle form. Here, the irregularly crushed form refers to a particle in a crushed form in which the form is not regular. As compared with a spherical particle obtained by inverse suspension polymerization or vapor phase polymerization, the form of the irregularly crushed form is not regular, and thus the mixability with a hydrophilic fiber such as pulp is excellent, and the liquid diffusibility due to gaps between particles is high; and thus the irregularly crushed form is preferable. The particulate water-absorbing agent according to one embodiment of the present invention is preferably a pulverized product in aqueous solution polymerization. The irregularly crushed form is obtained by pulverizing a gel or a dried product (preferably a dried product) of a crosslinked polymer obtained through aqueous solution polymerization. On the other hand, in the case of not undergoing the pulverizing step, a spherical particle or a granulated product of a spherical particle typically obtained by inverse suspension polymerization, droplet polymerization that, for example, sprays and polymerizes a polymerization monomer, or the like is not in an irregularly crushed form. In the embodiment of the present invention, when the form of the particulate water-absorbing agent is an irregularly crushed form, this particulate water-absorbing agent is superior in water absorption speed and RCAP to one having a high average roundness (for example, a spherical one). In the embodiment of the present invention, the average roundness of the particulate water-absorbing agent is preferably 0.70 or less, more preferably 0.60 or less, and further preferably 0.55 or less.

The method for calculating the average roundness is as follows. 100 or more particulate water-absorbing agents were randomly selected, and each particulate water-absorbing agent was photographed using an electron microscope (VE-9800 manufactured by KEYENCE CORPORATION) (magnification of 50 times) to obtain an image of the particulate water-absorbing agent, and the perimeter and the area were calculated for each particle using the attached image analysis software. Using the following expression:

$$\text{Roundness} = 4 \times \pi \times \text{area} / (\text{perimeter})^2 \quad \text{[Expression 2]}$$

the roundness of each particle is determined, and the average value of the obtained values is calculated as the average roundness.

(2-9) Water Insoluble Inorganic Particle/Water Soluble Polyvalent Metal Cation-Containing Compound The particulate water-absorbing agent of the present invention preferably further includes at least one selected from the group consisting of a water insoluble inorganic particle and a water soluble polyvalent metal cation-containing compound.

When the particulate water-absorbing agent includes a water insoluble inorganic particle, the fluidity after moisture absorption of the particulate water-absorbing agent can be improved. In addition, by adding a water insoluble inorganic particle, the absorption capacity of an absorbent article can be improved. Further, a water-absorbing resin particle (composition) may lose the fluidity thereof because of storage thereof after the production before an absorbent article is produced. By mixing a water insoluble inorganic particle into such a water-absorbing resin particle (composition) that has lost the fluidity to suitably shape an absorbent body, the fluidity of the water-absorbing resin particle (composition) is restored while maintaining the performance, and thus the productivity is improved. Here, the fluidity after moisture absorption refers to the fluidity of a particulate water-absorbing agent when stored under a high humidity condition, and the fluidity of a particulate water-absorbing agent including a water-absorbing resin is generally reduced by moisture absorption. A water insoluble inorganic particle has been added for the purpose of improving the fluidity after moisture absorption of a particulate water-absorbing agent, but the relationship of the expression (1) cannot be satisfied simply by adding and mixing a water-insoluble inorganic particle, and the Re-Wet under pressure in a swollen state of the particulate water-absorbing agent increases (see Comparative Examples described later). On the other hand, by devising an addition/mixing condition (for example, the mixing time) of the water insoluble inorganic particle or the like, the particulate water-absorbing agent can satisfy the relationship of the expression (1), and the liquid return under pressure in a swollen state of the particulate water-absorbing agent can be significantly suppressed.

Examples of the water insoluble inorganic particle include a multi-component metal compound such as hydrotalcite, silicon dioxide (silica), aluminum hydroxide, titanium dioxide, aluminum oxide, magnesium oxide, zinc oxide, talc, a metal phosphate (for example, a calcium phosphate such as tricalcium phosphate, barium phosphate, or aluminum phosphate), a metal borate (for example, titanium borate, aluminum borate, iron borate, magnesium borate, manganese borate, or calcium borate), silicic acid or a salt thereof, clay, diatomaceous soil, zeolite, bentonite, kaolin, and activated clay. Among these, the water insoluble inorganic particle preferably includes at least one kind selected from a multi-component metal compound, silicon dioxide, talc, and tricalcium phosphate, and more preferably includes at least one kind selected from silicon dioxide, aluminum hydroxide, and tricalcium phosphate, because the advantageous effect of the present invention can be remarkably obtained.

The volume average particle diameter of the water insoluble inorganic particle is preferably 10 μm or less, more preferably 5 μm or less, and further preferably 1 μm or less. In addition, the volume average particle diameter is preferably 0.05 μm or more, more preferably 0.1 μm or more, and further preferably 0.3 μm or more. When the volume average particle diameter is equal to or more than the above lower limit, it is possible to suppress a decrease in workability during the addition step and obtain sufficient performance. The volume average particle diameter of the water insoluble inorganic particle can be measured by a "laser diffraction/scattering method" (measured using a particle size analyzer, for example, trade name: Microtrac MT3000II, manufactured by Nikkiso Co., Ltd.).

The water insoluble inorganic particle may be surface treated. Examples of a surface treatment agent used for the surface treatment include specific examples of the surface treatment agent of the multi-component metal compound described below.

The above multi-component metal compound refers to a multi-component metal compound containing two metal cations, divalent and trivalent, and a hydroxyl group.

Examples of the divalent metal cation include $Mg^{2+}$, $Fe^{2+}$, $Zn^{2+}$, $Ca^{2+}$, $Ni^{2+}$, $Co^{2+}$, and $Cu^{2+}$, and $Mg^{2+}$ is preferable from the viewpoint of heat resistance and the like. Examples of the trivalent metal cation include $Al^{3+}$, $Fe^{3+}$, and $Mn^{3+}$, and $Al^{3+}$ is preferable from the viewpoint of heat resistance and the like. Therefore, in a suitable embodiment of the multi-component metal compound, the divalent metal cation is a magnesium cation and the trivalent metal cation is an aluminum cation.

The multi-component metal compound preferably has a hydrotalcite-like structure known as a structure of a layered compound represented by the general formula (1) $[M_1^{2+}{}_{1-x} M_2^{3+}{}_x (OH^-)_2]^{x+} \cdot [(A^{n-})_{x/n} \cdot mH_2O]^{x-}$ wherein $M_1^{2+}$ represents a divalent metal cation, $M_2^{3+}$ represents a trivalent metal cation, $A^{n-}$ represents an n-valent anion, and $H_2O$ represents water.

In addition, for the ratio of the divalent metal cation and the trivalent metal cation in the general formula (1), x is preferably in the range of 0.2 to 0.75, more preferably in the range of 0.25 to 0.7, and further preferably in the range of 0.25 to 0.5. In addition, examples of the anion include $OH^-$, $F^-$, $Cl^-$, $Br^-$, $NO_3^-$, $CO_3^{2-}$, $SO_4^{2-}$, $Fe(CN)_6^{3-}$, $CH_3COO^-$, an oxalate ion, or a salicylate ion, and a carbonate anion is preferable. In addition, m is a real number larger than 0, and it is preferable that $0<m\leq10$.

The form of the multi-component metal compound is not particularly limited, and is preferably a spherical form (including a powder form). In addition, the multi-component metal compound preferably has a constant particle size, and the volume average particle diameter thereof is preferably 2 μm or less, more preferably 1.5 μm or less, and further preferably 1 μm or less. When the particle diameter is equal to or less than the above upper limit, the amount added to obtain a sufficient effect does not become too large, and there is little possibility that the water absorption performance of the obtained water-absorbing agent is impaired. In addition, the volume average particle diameter is preferably 0.05 μm or more, more preferably 0.1 μm or more, and further preferably 0.3 μm or more. When the volume average particle diameter is equal to or more than the above lower limit, it is possible to suppress a decrease in workability during the addition step and obtain sufficient performance. In addition, the average particle diameter of the multi-component metal compound adhering to the surface of the water-absorbing resin particle can be measured by a measuring method using an SEM (scanning electron microscope).

Further, an organic compound may be intercalated between layers, and surface treatment for enhancing the mixability with the water-absorbing resin particle or the like may be applied.

Examples of a preferable structural formula of the multi-component metal compound include $Mg_6Al_2(OH)_{16}CO_3 \cdot 4H_2O$ and $Mg_4Al_2(OH)_{12}CO_3 \cdot 3H_2O$. Specific examples thereof include DHT-4H and DHT-6 manufactured by Kyowa Chemical Industry Co., Ltd., and STABIACE HT-1-NC and STABIACE HT-P manufactured by Sakai Chemical Industry Co., Ltd.

The content of the water insoluble inorganic particle is 0.01% by weight or more and less than 10% by weight, and preferably 0.1 to 5% by weight per 100% by weight of the polyacrylic acid (salt)-based water-absorbing resin from the viewpoint of improving the absorption amount of an absorbent article and providing an excellent balance between the absorption amount and the Re-Wet.

When the particulate water-absorbing agent includes a water-soluble polyvalent metal cation-containing compound, the performance of the water-absorbing agent is improved. A water-soluble polyvalent metal cation-containing compound has been added for the purpose of improving the fluidity after moisture absorption of a particulate water-absorbing agent, but by devising an addition/mixing condition (for example, the mixing time) of a water-soluble polyvalent metal cation-containing compound or the like instead of simply adding and mixing a water-soluble polyvalent metal cation-containing compound, the relationship of the expression (1) can be satisfied and a particulate water-absorbing agent exhibiting sufficient water absorption performance under pressure can be obtained.

The water-soluble polyvalent metal cation-containing compound refers to a compound other than a multi-component metal compound containing a divalent or higher, preferably trivalent or higher, metal cation. Examples of the trivalent or higher metal cation include aluminum, zirconium, and titanium, and aluminum is preferable. Examples of the water-soluble polyvalent metal cation-containing compound include a polyvalent metal compound such as an inorganic salt of a polyvalent metal such as aluminum sulfate, aluminum chloride, zirconium chloride oxide, zirconium ammonium carbonate, zirconium potassium carbonate, zirconium potassium carbonate, zirconium sulfate, zirconium acetate, or zirconium nitrate, or an organic salt of a polyvalent metal such as aluminum acetate, aluminum lactate, zirconium hydroxychloride, titanium triethanolaminate, or titanium lactate. Among these, the water-soluble polyvalent metal cation-containing compound is preferably a compound containing aluminum as a polyvalent metal cation, and more preferably aluminum sulfate, potassium aluminum sulfate, or sodium aluminum sulfate.

The content of the water-soluble polyvalent metal cation-containing compound is preferably 0.001 to 5 parts by weight, more preferably 0.01 to 2 parts by weight, and further preferably 0.01 to 1 part by weight in terms of the amount of the polyvalent metal cation per 100 parts by weight of the polyacrylic acid (salt)-based water-absorbing resin from the viewpoint of improving the performance of the water-absorbing agent.

The particulate water-absorbing agent of the above embodiment can be obtained, for example, by controlling in such a way as to satisfy the expression (1) in the following production methods (a) to (c).

(Production Method a)

A water insoluble inorganic particle is added to a water-absorbing resin, and the mixing time is controlled to obtain a particulate water-absorbing agent satisfying the expression (1).

The water-absorbing resin to which the water insoluble inorganic particle is added may be surface crosslinked or may not be surface crosslinked. In addition, the water insoluble inorganic particle may be mixed with a water-absorbing resin composition containing a water-absorbing resin or another additive. Further, when an absorbent article is produced, the water-absorbing resin (composition), the water insoluble inorganic particle, and a hydrophilic fiber may be mixed.

In addition, the water-absorbing resin and the water insoluble inorganic particle are preferably dry-mixed. Dry mixing is preferable because the amount of dust of the water-absorbing agent obtained is reduced. The dry mixing means mixing in a state in which a liquid substance other than the liquid substance absorbed or retained by a water insoluble inorganic particle and a water-absorbing resin is substantially absent (preferably absent). Specifically, the dry mixing compasses a formation in which a water insoluble inorganic particle including absorbed moisture or an organic compound retained between layers, and a water-absorbing resin having a dry residue, absorbed moisture, a surface crosslinking agent added in the surface crosslinking agent addition step, a solvent, or the like are mixed without further adding a liquid substance.

The mixing time of the water-absorbing resin and the water insoluble inorganic particle is not particularly limited and is appropriately set according to the mixing apparatus, and the mixing is preferably carried out for a relatively long time so as to satisfy the above expression (1). That is, in the present invention, a time longer than the mixing time for the purpose of simply mixing an additive is preferably set to mix the water-absorbing resin and the water insoluble inorganic particle. Usually, for the purpose of improving productivity, the operation of the mixing apparatus is stopped when it can be confirmed visually or by a conventional evaluation method that the additive is uniformly mixed. In addition, even by such conventional mixing, the basic performance required for particulate water-absorbing agents such as AAP and CRC is guaranteed. However, in these particulate water-absorbing agents, the Re-Wet under pressure in a swollen state of the particulate water-absorbing agents is not sufficiently reduced. The present inventors have known and studied such a problem and as a result, hypothesized that the water insoluble inorganic particle easily aggregates and thus is not sufficiently dispersed microscopically in the water-absorbing resin, leading to a decrease in a physical property of the particulate water-absorbing agent and particularly an increase in the Re-Wet under pressure in a swollen state when the water insoluble inorganic particle is added. Then, the present inventors have found that a particulate water-absorbing agent for satisfying the expression (1) can be obtained by making the mixing time when mixing the water insoluble inorganic particle longer than the time required for usual uniform mixing. In general, the time required for uniform mixing has been set by a conventional evaluation method or the like, but the present inventors have found RCAP, which is a novel parameter serving as one index of improving the Re-Wet under pressure in a swollen state, and for the first time thereby, the present inventors have discovered an additional effect of further lengthening the mixing time, which was previously considered sufficient. Conventionally, a long mixing time has been considered to cause a decrease in productivity or the like and be rather unfavorable, and thus has not been actively implemented, but in the present invention, by the above discovery, a merit that more than outweighs demerits such as a decrease in productivity has been able to be found. The mixing time of the water-absorbing resin and the water insoluble inorganic particle is, for example, 5 minutes or more, preferably 15 minutes or more, and more preferably 30 minutes or more.

The unit used for mixing the water-absorbing resin and the water insoluble inorganic particle is not particularly limited, and it is preferable to use a mixing unit that does not provide a gentle stirring as provided by a paddle type stirring apparatus, but involves a relatively strong stirring condition.

The upper limit of the mixing time is not particularly limited, and in consideration of productivity and saturation of the effect, the upper limit is preferably 5 hours or less and more preferably 2 hours or less. In addition, the mixing method is not particularly limited, and a method for mixing while applying vibration, a method for mixing while rotating (for example, a method using a Turbula shaker mixer), mixing using a stirrer, or a method involving transporting a particle along with airflow such as air transport is preferable. The stirring conditions are appropriately set according to the mixing apparatus, and for example, when a Turbula shaker mixer is used, the rotation speed is preferably higher than 45 rpm, more preferably 70 rpm or more, and further preferably 100 rpm or more. In addition, the mixing time required for ideal mixing differs depending on each mixing method, and the object of the present application can be achieved by appropriately adjusting the mixing time. One index of determining whether or not the object of the present application has been achieved can be whether or not the physical property parameters of the present application are satisfied.

(Production Method b)

A water soluble polyvalent metal cation-containing compound is added to a water-absorbing resin, and the mixing time is controlled to obtain a particulate water-absorbing agent satisfying the expression (1).

The water soluble polyvalent metal cation-containing compound may be directly mixed as a powder into the water-absorbing resin, may be mixed as a solution, particularly an aqueous solution, or may be dissolved in a surface crosslinking agent or an aqueous solution thereof and mixed.

In addition, the water soluble polyvalent metal cation-containing compound may be added a plurality of times, and in this case, for example, when the water soluble polyvalent metal cation-containing compound is added twice, the (weight) ratio is defined in the range of 1/99 to 99/1 and preferably 10/90 to 90/10. A (weight) ratio exceeding these ranges is not preferable because the situation is extremely close to that of one-time addition and the effect of multiple additions becomes poor.

The method for adding a water soluble polyvalent metal cation-containing compound is not particularly limited, and preferably, the water soluble polyvalent metal cation-containing compound is (1) added at the same time as the addition of a surface crosslinking agent (added in the surface crosslinking step), or (2) added after the surface crosslinking step. By adding the water soluble polyvalent metal cation-containing compound at such a timing, the compound can be caused to be present in the vicinity of the particle surface, and the performance of the water-absorbing agent can be improved. When the water soluble polyvalent metal cation-containing compound is added after the surface crosslinking step, the compound may be added together with another additive.

The water soluble polyvalent metal cation-containing compound may be added to the water-absorbing resin (powder) in the state of a solution in which the compound is dissolved in a solvent (for example, water). When the water soluble polyvalent metal cation-containing compound is added as an aqueous solution, a hydrophilic organic solvent (alcohol or polyglycol) or a surfactant in addition to water may be used in combination to improve dispersibility, solubility, and mixability. The amount of water used is appropriately determined depending on the type of the water soluble polyvalent metal cation-containing compound and the addition method, and for example, is 0 parts by weight (dry mixing) to 50 parts by weight, further 0.1 to 10 parts by weight, or 0.5 to 5 parts by weight per 100 parts by weight of the water-absorbent resin.

In addition, the water soluble polyvalent metal cation-containing compound may be added as it is to the water-absorbing resin (powder). In this case, the water soluble polyvalent metal cation-containing compound is preferably in the formation of a particle. The volume average particle diameter of the water soluble polyvalent metal cation-containing compound is preferably 10 m or less, more preferably 5 m or less, and further preferably 1 μm or less. In addition, the volume average particle diameter is preferably 0.05 m or more, more preferably 0.1 m or more, and further preferably 0.3 m or more. When the volume average particle diameter is equal to or more than the above lower limit, it is possible to suppress a decrease in workability during the addition step and obtain sufficient performance. The volume average particle diameter of the water soluble polyvalent metal cation-containing compound can be measured by a "laser diffraction/scattering method" (measured using a particle size analyzer, for example, trade name: Microtrac MT3000II, manufactured by Nikkiso Co., Ltd.).

As used herein, water soluble refers to a substance that is soluble (or easily soluble) in water at room temperature (23° C.) and under normal pressure (under 1 atm). For example, water soluble refers to a substance that exhibits an amount dissolved of 1 g or more in 100 ml of water at room temperature and normal pressure. In addition, water insoluble refers to a substance that is insoluble (or sparingly soluble) in water at room temperature (23° C.) and under normal pressure (under 1 atm). For example, water insoluble refers to a substance that exhibits an amount dissolved of less than 1 g in 100 ml of water at room temperature and normal pressure, and further the amount dissolved in 100 ml of water at room temperature and normal pressure is preferably less than 0.1 g.

The mixing time of the water-absorbing resin and the water soluble polyvalent metal cation-containing compound is not particularly limited and is appropriately set according to the mixing apparatus, and the mixing is preferably carried out for a relatively long time so as to satisfy the above expression (1). That is, in the present invention, a time longer than the mixing time for the purpose of simply mixing an additive is preferably set to mix the water-absorbing resin and the water soluble polyvalent metal cation-containing compound. Usually, for the purpose of improving productivity, the operation of the mixing apparatus is stopped when it can be confirmed visually or by a conventional evaluation method that the additive is uniformly mixed. In addition, even by such conventional mixing, the basic performance required for particulate water-absorbing agents such as AAP and CRC is guaranteed. However, in these particulate water-absorbing agents, the Re-Wet under pressure in a swollen state of the particulate water-absorbing agents has not been sufficiently reduced.

The present inventors have known and studied such a problem and as a result, hypothesized that a conventional mixing method and time is inadequate and thus the water soluble polyvalent metal cation-containing compound is not sufficiently dispersed microscopically in the water-absorbing resin, leading to a decrease in a physical property of the particulate water-absorbing agent and particularly an increase in the Re-Wet under pressure in a swollen state when the water soluble polyvalent metal cation-containing compound is added. Then, the present inventors have found that a particulate water-absorbing agent for satisfying the expression (1) can be obtained by making the mixing time when mixing the water soluble polyvalent metal cation-containing compound longer than the time required for usual uniform mixing. In general, the time required for uniform mixing has been set by a conventional evaluation method or the like, but the present inventors have found RCAP, which is a novel parameter serving as one index of improving the Re-Wet under pressure in a swollen state, and for the first time thereby, the present inventors have discovered an additional effect of further lengthening the mixing time, which was previously considered sufficient. Conventionally, a long mixing time has been considered to cause a decrease in productivity or the like and be rather unfavorable, and thus has not been actively implemented, but in the present invention, by the above discovery, a merit that more than outweighs demerits such as a decrease in productivity has been able to be found. The mixing time of the water-absorbing resin and the water soluble polyvalent metal cation-containing compound is, for example, 5 minutes or more, preferably 15 minutes or more, and more preferably 30 minutes or more. The upper limit of the mixing time is not particularly limited, and in consideration of productivity and saturation of the effect, the upper limit is preferably 5 hours or less, and more preferably 2 hours or less. In addition, the mixing method is not particularly limited, and a method for mixing while applying vibration, a method for mixing while rotating (for example, a method using a Turbula shaker mixer), mixing using a stirrer, or a method involving transporting a particle along with airflow such as air transport is preferable. The rotation speed in this case may be the same as that in production method a. In addition, the mixing time required for ideal mixing differs depending on each mixing method, and the object of the present application can be achieved by appropriately adjusting the mixing time. One index of determining whether or not the object of the present application has been achieved can be whether or not the physical property parameters of the present application are satisfied.

(Production Method c)

The production method for producing a particulate water-absorbing agent has a step of washing the water-absorbing resin with a washing liquid including water as a main component. By washing the water-absorbing resin with a washing liquid including water as a main component, a particulate water-absorbing agent satisfying the expression (1) can be easily obtained. Although the detailed mechanism is unknown, it is considered that this is because by washing the water-absorbing resin with a washing liquid including water as a main component, the water-absorbing resin is brought into a swollen state by containing water, and by washing in this state, an unnecessary component that can affect the water-absorbing performance can be efficiently washed away and a water-absorbing agent having a high RCAP can be easily obtained.

In the above Patent Literature 2 (International Publication No. WO 97/003114), washing is carried out for the purpose of reducing the residual crosslinking agent, and the literature recites "the mixed ratio of water and hydrophilic organic solvent is selected such that the water absorbent resin powders are not swollen with the mixed solution" and thus this step is clearly distinguished from the above step of swelling the water-absorbing resin powder by washing with a washing liquid including water as a main component.

As a washing method, for example, it is preferable to bring the water-absorbing resin into a swollen state and then wash the same with a washing liquid. Examples of the method for bringing the water-absorbing resin into a swollen state include a method involving using a liquid including water as a main component to immerse the water-absorbing resin in the liquid. The immersion time is not particularly limited as long as the water-absorbing resin is sufficiently swollen, and may be, for example, 1 minute or more, or 5 minutes or more.

The inclusion of water as a main component means that the washing liquid includes water in an amount of 80% by weight or more, preferably 90% by weight or more, more preferably 95% by weight or more, and further more preferably 99% by weight or more and preferably substantially consists of water.

The water preferably includes no impurities, is preferably RO water, deionized water, distilled water, purified water, or the like, and more preferably deionized water or distilled water.

A hydrophilic organic solvent may be included as a component other than water. Suitable examples of the hydrophilic organic solvent used include a lower alcohol such as methyl alcohol, ethyl alcohol, propyl alcohol, isopropyl alcohol, and t-butyl alcohol.

Here, the water-absorbing resin may be either a water-absorbing resin powder before surface crosslinking treatment or a water-absorbing resin particle after surface crosslinking treatment, and the water-absorbing resin powder before surface crosslinking treatment (so-called base polymer) is preferably washed because a particulate water-absorbing agent satisfying the expression (1) can be more easily obtained.

The washing method is not particularly limited, and the water-absorbing resin can be washed by a continuous or discontinuous batch method with the washing liquid. Examples thereof include a method involving contacting the water-absorbing resin with a washing liquid with stirring as necessary therein, and then separating the water-absorbing resin from the washing liquid by, for example, decantation or suction filtration; and water-passing washing involving passing a washing liquid through a hydrogel in a swollen state.

In addition, the washing may be carried out a plurality of times.

In these methods, the washing time (water passing time) is preferably 15 minutes to 10 hours, more preferably 30 minutes to 8 hours, and further more preferably 1 to 5 hours. The temperature of the washing liquid is preferably 20 to 50° C. from the viewpoint of washing effect. In addition, the pressure during the washing is not particularly limited to pressurization, depressurization, or normal pressure, and the washing is usually carried out under normal pressure.

The water-absorbing resin (hydrogel) after washing may be further additionally subjected to a step of drying, pulverizing, classification, or the like as necessary, as in the subsequent steps of the hydrogel in [3] Method for producing particulate water-absorbing agent below.

[3] Method for Producing Particulate Water-Absorbing Agent

Production steps (3-1) to (3-8) of the particulate water-absorbing agent according to the present invention will be shown below.

(3-1) Step for Preparing Aqueous Monomer Solution

The present step is a step of preparing an aqueous solution (hereinafter, referred to as an "aqueous monomer solution") including a monomer (for example, acrylic acid (salt)) as a main component. A monomer slurry solution can also be used as long as the water absorption performance of the water-absorbing resin obtained is not reduced, but in this section, the aqueous monomer solution will be described for convenience.

In addition, the above "main component" means that the amount (content) of the acrylic acid (salt) used is usually 50 mol % or more, preferably 70 mol % or more, and more preferably 90 mol % or more (the upper limit is 100 mol %) based on the total amount of the monomers (excluding an internal crosslinking agent) used for polymerization reaction of the water-absorbing resin.

(Acrylic Acid)

In the present invention, acrylic acid and/or a salt thereof (hereinafter, referred to as "acrylic acid (salt)") is used as a monomer from the viewpoint of a physical property and productivity of the particulate water-absorbing agent obtained.

The above "acrylic acid" may be known acrylic acid, and may include preferably a methoxyphenol and more preferably p-methoxyphenol as a polymerization inhibitor in an amount of preferably 200 ppm or less, more preferably 10 to 160 ppm, and further preferably 20 to 100 ppm from the viewpoint of the polymerizability of the acrylic acid and the color tone of the particulate water-absorbing agent. In addition, for an impurity in acrylic acid, the compounds described in US Patent Application Publication No. 2008/0161512 are also applied to the present invention.

In addition, the above "acrylic acid salt" is obtained by neutralizing the above acrylic acid with the following basic composition, but the acrylic acid salt may be a commercially available acrylic acid salt (for example, sodium acrylate) or may be obtained by neutralizing in a production plant of the particulate water-absorbing agent.

(Basic Composition)

In the present invention, the "basic composition" refers to a composition containing a basic compound, and corresponds to, for example, a commercially available sodium hydroxide aqueous solution.

Specific examples of the basic compound include a carbonate or a hydrogencarbonate of an alkali metal, a hydroxide of an alkali metals, ammonia, and an organic amine. Among these, the basic compound is desired to be strongly basic from the viewpoint of a physical property of the particulate water-absorbing agent obtained. That is, a hydroxide of an alkali metal such as sodium hydroxide, potassium hydroxide, or lithium hydroxide is preferable, and sodium hydroxide is more preferable.

(Neutralization)

As the neutralization in the present invention, either neutralization of acrylic acid (before polymerization) or neutralization of a crosslinked hydrogel polymer obtained by crosslinking and polymerizing acrylic acid (after polymerization) (hereinafter, referred to as "post-neutralization") can be selected or the both can be used in combination. In addition, these neutralizations may be a continuous type or a batch type and are not particularly limited, and the continuous type is preferable from the viewpoint of production efficiency and the like.

Regarding conditions such as an apparatus for neutralizing, the neutralization temperature, and the residence time, the conditions described in International Publication No. WO 2009/123197 and US Patent Application Publication No. 2008/0194863 are also applied to the present invention.

The rate of neutralization in the present invention is preferably 10 to 90 mol %, more preferably 40 to 85 mol %, further preferably 50 to 80 mol %, and particularly preferably 60 to 75 mol % based on the acid group of the monomer. If the rate of neutralization is less than 10 mol %, the fluid retention capacity may be remarkably reduced. On the other hand, if the rate of neutralization exceeds 90 mol %, a water-absorbing resin having a high fluid retention capacity under pressure may not be obtained.

The rate of neutralization is also the same in the case of post-neutralization. In addition, the above rate of neutralization is also applied to the rate of neutralization of the particulate water-absorbing agent as a final product. A rate of neutralization of 75 mol % means a mixture of 25 mol % of acrylic acid and 75 mol % of an acrylic acid salt. In addition, the mixture may be referred to as a partially neutralized acrylic acid.

(Another Monomer)

In the present invention, "another monomer" refers to a monomer other than the above acrylic acid (salt), and another monomer can be used in combination with acrylic acid (salt) to produce a particulate water-absorbing agent.

Examples of the another monomer include a water soluble or hydrophobic unsaturated monomer. Specifically, the compounds described in US Patent Application Publication No. 2005/0215734 (excluding acrylic acid) are also applied to the present invention.

(Internal Crosslinking Agent)

As the internal crosslinking agent used in the present invention, the compounds described in U.S. Pat. No. 6,241,928 are also applied to the present invention. From these, one or two or more compounds are selected in consideration of reactivity. In the present invention, it is preferable to surface treat a crosslinked product using an internal crosslinking agent in consideration of water absorption performance.

In addition, from the viewpoint of the water absorption performance or the like of the water-absorbing resin obtained, preferably a compound having two or more polymerizable unsaturated groups, more preferably a compound having a thermal degradation property at the following drying temperature, and further preferably a compound having two or more polymerizable unsaturated groups having a (poly)alkylene glycol structural unit are used as the internal crosslinking agent.

Examples of the polymerizable unsaturated group include preferably an allyl group, a (meth)acrylate group, and more preferably a (meth)acrylate group. In addition, polyethylene glycol is preferable as the (poly)alkylene glycol structural unit, and the number n is preferably 1 to 100 and more preferably 6 to 50.

Therefore, in the present invention, (poly)alkylene glycol di(meth)acrylate or (poly)alkylene glycol tri(meth)acrylate is preferably used, and (poly)ethylene glycol di(meth)acrylate is more preferably used.

The amount of the internal crosslinking agent used is preferably 0.0001 to 10 mol % and more preferably 0.001 to 1 mol % based on the total amount of the monomers. By setting the amount used within the above range, a desired water-absorbing resin can be obtained. If the amount used is too small, the gel strength tends to decrease and the water soluble component tends to increase, and if the amount used is too large, the fluid retention capacity tends to decrease.

In the present invention, a method involving adding a predetermined amount of an internal crosslinking agent to an aqueous monomer solution in advance and carrying out a crosslinking reaction at the same time as polymerization is preferably applied. On the other hand, in addition to this method, a method involving adding an internal crosslinking agent during or after polymerization for post-crosslinking, a method involving radical crosslinking using a radical polymerization initiator, a method involving radiation crosslinking using an active energy ray such as an electron beam or an ultraviolet ray, or the like can also be adopted. In addition, these methods can also be used in combination.

(Another Substance Added to Aqueous Monomer Solution)

In the present invention, the following substances can also be added at the time of preparation of the aqueous monomer solution from the viewpoint of improving a physical property of the water-absorbing resin obtained.

Specifically, a hydrophilic polymer such as starch, a starch derivative, cellulose, a cellulose derivative, polyvinyl alcohol, polyacrylic acid (salt), or a polyacrylic acid (salt) crosslinked product can be added in an amount of preferably 50% by weight or less, more preferably 20% by weight or less, further preferably 10% by weight or less, and particularly preferably 5% by weight or less (the lower limit is 0% by weight) in a aqueous monomer solution, and a foaming agent such as a carbonate, an azo compound, or a bubble, a surfactant, a chelating agent such as diethylenetriaminepentaacetic acid (salt) or ethylenediaminetetramethylenephosphonic acid (salt), a chain transfer agent, or the like can be added in an amount of preferably 5% by weight or less, more preferably 1% by weight or less, and further preferably 0.5% by weight or less (the lower limit is 0% by weight) in a aqueous monomer solution.

In addition, the above substances may be added not only in the formation of being added to the aqueous monomer solution but also in the formation of being added in the course of the polymerization, or these formations can also be used in combination.

When a water soluble resin or a water-absorbing resin is used as the hydrophilic polymer, a graft polymer or a water-absorbing resin composition (for example, starch-acrylic acid polymer or PVA-acrylic acid polymer) can be obtained. These polymers and water-absorbing resin composition are also within the scope of the present invention.

(Concentration of Monomer Component)

In the present step, each of the above substances is added when preparing an aqueous monomer solution. The concentration of the monomer component in the aqueous monomer solution is not particularly limited, and is preferably 10 to 80% by weight, more preferably 20 to 75% by weight, and further preferably 30 to 70% by weight from the viewpoint of a physical property of the water-absorbing resin.

In addition, when aqueous solution polymerization or inverse suspension polymerization is adopted, a solvent other than water can be used in combination as necessary. In this case, the type of the solvent is not particularly limited.

The above "concentration of the monomer component" is a value determined by the following expression (5), and the weight of the aqueous monomer solution do not include the weight of a graft component, a water-absorbing resin, and a hydrophobic solvent in inverse suspension polymerization.

$$\text{(Concentration of monomer component (\% by weight))} = \text{(Weight of monomer component)} / \text{(Weight of aqueous monomer solution)} \times 100 \qquad \text{Expression (5)}$$

(3-2) Polymerization Step

The present step is a step of polymerizing the acrylic acid (salt)-based aqueous monomer solution obtained in the above step for preparing a aqueous monomer solution to obtain a crosslinked hydrogel polymer (hereinafter, referred to as a "hydrogel").

(Polymerization Initiator)

The polymerization initiator used in the present invention is appropriately selected depending on the polymerization formation and the like and thus is not particularly limited, and examples thereof include a thermal degradation type polymerization initiator, a photodegradation type polymerization initiator, or a redox-based polymerization initiator in which a reducing agent that promotes degradation of these polymerization initiators is used in combination. Specifically, one kind or two or more kinds of the polymerization initiators disclosed in U.S. Pat. No. 7,265,190 are used. From the viewpoint of the handleability of the polymerization initiator and a physical property of the particulate water-absorbing agent or the water-absorbing resin, preferably a peroxide or an azo compound, more preferably a peroxide, and further preferably a persulfate is used.

The amount of the polymerization initiator used is preferably 0.001 to 1 mol % and more preferably 0.001 to 0.5 mol % based on the monomer. In addition, the amount of the reducing agent used is preferably 0.0001 to 0.02 mol % based on the monomer.

Instead of the above polymerization initiator, the polymerization reaction may be carried out by irradiating with an active energy ray such as a radiation, an electron beam, or an ultraviolet ray, or these active energy rays and the polymerization initiator may be used in combination.

(Polymerization Mode)

The polymerization mode applied to the present invention is not particularly limited, and is preferably spray droplet polymerization, aqueous solution polymerization, or inverse suspension polymerization, and more preferably aqueous solution polymerization or inverse suspension polymerization, and further preferably aqueous solution polymerization, from the viewpoint of a water absorption property, ease of polymerization control, and the like. Among these, continuous aqueous solution polymerization is particularly preferable, and either continuous belt polymerization or continuous kneader polymerization is applied.

As a specific polymerization formation, continuous belt polymerization is disclosed in U.S. Pat. Nos. 4,893,999, 6,241,928, US Patent Application Publication No. 2005/215734, and the like, and continuous kneader polymerization is disclosed in U.S. Pat. Nos. 6,987,151, 6,710,141, and the like. By adopting these continuous aqueous solution polymerizations, the production efficiency of the water-absorbing resin is improved.

In addition, examples of a preferable mode of the above continuous aqueous solution polymerization include "high temperature start polymerization" and "high concentration polymerization." The "high temperature start polymerization" refers to a mode in which polymerization is started at a temperature of the aqueous monomer solution of preferably 30° C. or more, more preferably 35° C. or more, further preferably 40° C. or more, and particularly preferably 50° C.

or more (the upper limit is the boiling point), and the "high concentration polymerization" refers to a formation in which polymerization is carried out at a monomer concentration of preferably 30% by weight or more, more preferably 35% by weight or more, further preferably 40% by weight or more, and particularly preferably 45% by weight or more (the upper limit is the saturation concentration). These polymerization modes can also be used in combination.

In addition, in the present invention, polymerization can also be carried out in an air atmosphere, and from the viewpoint of the color tone of the water-absorbing resin obtained, the polymerization may be carried out in an atmosphere of an inert gas such as nitrogen or argon. In this case, for example, the oxygen concentration is preferably controlled to 1% by volume or less. The dissolved oxygen in the aqueous monomer solution is also preferably displaced with an inert gas (for example, dissolved oxygen; less than 1 mg/l).

In addition, in the present invention, it is also possible to carry out foam polymerization in which a bubble (particularly the above inert gas or the like) is dispersed in a aqueous monomer solution to carry out polymerization.

In addition, in the present invention, the concentration of solids content may be increased during the polymerization. The degree of solids content increase is defined by the following expression (6) as an index of such an increase in concentration of solids content. The degree of increase in concentration of solids content is preferably 1% by weight or more and more preferably 2% by weight or more.

$$\text{(Degree of increase in solids content (\% by weight))} = \text{(Concentration of solids content of hydrogel after polymerization (\% by weight))} - \text{(Concentration of solids content of aqueous monomer solution (\% by weight))} \quad \text{Expression (6)}$$

However, the concentration of solids content of the aqueous monomer solution is a value determined by the following expression (7), and components in the polymerization system are the aqueous monomer solution and a graft component, the water-absorbing resin, and other solids (for example, a water insoluble fine particle) and does not encompass a hydrophobic solvent in inverse suspension polymerization.

$$\text{(Solids content (\% by weight) of aqueous monomer solution)} = \text{(Weight of (monomer component + graft component + water-absorbing resin + other solids))} / \text{(Weight of components in polymerization system)} \times 100 \quad \text{Expression (7)}$$

In addition, as a formation of aqueous solution polymerization, the present invention can be carried out by a stationary polymerization method in which a aqueous monomer solution is polymerized in a stationary state, a stirring polymerization method in which a aqueous monomer solution is polymerized within a stirring apparatus, or the like. In the stationary polymerization method, an endless belt is preferably used. The belt is preferably a resin or rubber belt that does not easily release the heat of polymerization from the contact surface thereof.

(3-3) Gel-Crushing Step

The present step is a step of gel-crushing the hydrogel obtained in the above polymerization step using, for example, a screw extruder such as a kneader or a meat chopper or a gel crusher such as a cutter mill to obtain a hydrogel in a particulate form (hereinafter, referred to as a "particulate hydrogel"). When the above polymerization step is kneader polymerization, the polymerization step and the gel-crushing step are carried out at the same time. In addition, when a particulate hydrogel is directly obtained in the polymerization process as in vapor phase polymerization or inverse suspension polymerization, the gel-crushing step may not be carried out.

Regarding a gel crushing condition and a formation other than the above, the contents disclosed in International Publication No. WO 2011/126079 are preferably applied to the present invention.

(3-4) Drying Step

The present step is a step of drying the particulate hydrogel obtained in the above polymerization step and/or gel-crushing step to a desired solids content of the resin to obtain a dry polymer. The solids content of the resin is determined from an amount lost from drying (weight change when 1 g of the water-absorbing resin is heated at 180° C. for 3 hours), and is preferably 80% by weight or more, more preferably 85 to 99% by weight, further preferably 90 to 98% by weight, and particularly preferably 92 to 97% by weight.

The method for drying the particulate hydrogel is not particularly limited, and examples thereof include heat drying, hot air drying, vacuum drying, fluidized layer drying, infrared drying, microwave drying, drum dryer drying, drying by azeotropic dehydration with a hydrophobic organic solvent, and high-humidity drying using high temperature vapor. Among these, from the viewpoint of drying efficiency, hot air drying is preferable, and band drying in which hot air drying is carried out on a ventilation belt is more preferable.

The drying temperature (temperature of hot air) in the hot air drying is preferably 120 to 250° C. and more preferably 150 to 200° C. from the viewpoint of the color tone of the water-absorbing resin and the drying efficiency. Drying conditions other than the above drying temperature, such as the flow speed of hot air and the drying time, may be appropriately set according to the moisture content and the total weight of the particulate hydrogel subjected to drying and the target solids content of the resin, and when the band drying is carried out, the conditions described in International Publication No. WO 2006/100300, No. WO 2011/025012, No. WO 2011/025013, No. WO 2011/111657, or the like are appropriately applied.

(3-5) Pulverizing Step and Classification Step

The present step is a step of pulverizing the dry polymer obtained in the above drying step (pulverizing step), adjusting the same to a particle size in a predetermined range (classification step) to obtain a water-absorbing resin powder (a water-absorbing resin in a powder form before surface crosslinking is referred to as a "water-absorbing resin powder" for convenience).

Examples of the device used in the pulverizing step of the present invention include a high-speed rotary crusher such as a roll mill, a hammer mill, a screw mill, or a pin mill, a vibration mill, a knuckle type crusher, and a cylindrical mixer, and if necessary, these are used in combination.

In addition, the method for adjusting the particle size in the classification step of the present invention is not particularly limited, and examples thereof include sieve classification using a JIS standard sieve (JIS Z8801-1 (2000))

and air flow classification. The particle size adjustment of the water-absorbing resin is not limited to the above pulverizing step and classification step, and can appropriately be carried out in the polymerization step (particularly inverse suspension polymerization or spray droplet polymerization) or another step (for example, a granulating step or a fine powder recycling step).

The weight average particle diameter (D50) of the water-absorbing resin powder (water-absorbing resin powder before the surface crosslinking step, so-called base polymer) obtained in the above step is preferably 200 to 600 μm, more preferably 200 to 550 μm, and further preferably 250 to 500 μm. The proportion of a particle having a particle diameter of less than 150 μm is preferably 10% by weight or less, more preferably 5% by weight or less, and further preferably 1% by weight or less, and the proportion of a particle having a particle diameter of 850 μm or more is preferably 5% by weight or less, more preferably 3% by weight or less, and further preferably 1% by weight or less. In either case, a smaller lower limit of the proportion of the particle is more preferable, and the lower limit is desirably 0% by weight and may be about 0.1% by weight. Further, the logarithmic standard deviation ($\sigma\zeta$) of the particle size distribution is preferably 0.20 to 0.50, more preferably 0.25 to 0.40, and further preferably 0.27 to 0.35. These particle sizes are measured using a standard sieve according to the measuring method disclosed in U.S. Pat. No. 7,638,570 or EDANA ERT 420.2-02.

The above particle sizes are applied not only to the water-absorbing resin after surface crosslinking (hereinafter, sometimes referred to as a "water-absorbing resin particle" for convenience), but also to the particulate water-absorbing agent as a final product. Because of this, it is preferable to carry out surface crosslinking treatment (surface crosslinking step) so as to maintain the particle size of the water-absorbing resin in the above range, and the particle size is more preferably adjusted by providing a sizing step after the surface crosslinking step. particle is preferably subjected to (3-6) Surface Crosslinking Step The present step is a step of providing a portion having a higher crosslink density on the surface layer of the water-absorbing resin powder (a portion several tens of m deep from the surface of the water-absorbing resin powder) obtained through the above steps, and is composed of a mixing step, a heat treatment step, and a cooling step (optional).

In the surface crosslinking step, a water-absorbing resin (water-absorbing resin particle) surface crosslinked by radical crosslinking, surface polymerization, or a crosslinking reaction with a surface crosslinking agent on the surface of the water-absorbing resin powder or the like can be obtained.

(Surface Crosslinking Agent)

The surface crosslinking agent used in the present invention is not particularly limited, and examples thereof include an organic or inorganic surface crosslinking agent. Among these, an organic surface crosslinking agent that reacts with a carboxyl group is preferable from the viewpoint of a physical property of the water-absorbing resin and the handleability of the surface crosslinking agent. Examples thereof include one or two or more surface crosslinking agents disclosed in U.S. Pat. No. 7,183,456. More specific examples include a polyhydric alcohol compound, an epoxy compound, a haloepoxy compound, a polyvalent amine compound or a condensate thereof with a haloepoxy compound, an oxazoline compound, an oxazolidinone compound, a polyvalent metal salt, an alkylene carbonate compound, and a cyclic urea compound.

Specific examples of the organic surface crosslinking agent include a polyalcohol compound such as (di-, tri-, tetra-, or poly-)ethylene glycol, (di- or poly-)propylene glycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, di- or triethanolamine, pentaerythritol, or sorbitol; an epoxy compound as (poly)ethylene glycol diglycidyl ether, (di- or poly-)glycerol polyglycidyl ether, or glycidol; an oxazoline compound such as 2-oxazolidone, N-hydroxyethyl-2-oxazolidone, or 1,2-ethylenebisoxazoline; an alkylene carbonate compound such as 1,3-dioxolan-2-one (ethylene carbonate), 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, or 1,3-dioxopan-2-one; a haloepoxy compound such as epichlorohydrin, epibromohydrin, or α-methylepichlorohydrin, and a polyvalent amine adduct thereof (for example, KYMENE manufactured by Hercules Incorporated; registered trademark); a silane coupling agent such as γ-glycidoxypropyltrimethoxysilane or γ-aminopropyltriethoxysilane; an oxetane compound such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyloxetane, 3-chloromethyl-3-ethyloxetane, or a polyvalent oxetane compound; and a cyclic urea compound such as 2-imidazolidinone.

As the polyhydric alcohol, a polyhydric alcohol having 2 to 8 carbon atoms is preferable, a polyhydric alcohol having 3 to 6 carbon atoms is more preferable, and a polyhydric alcohol having 3 to 4 carbon atoms is further preferable. Further, a diol is preferable, examples thereof include ethylene glycol, propylene glycol, 1,3-propanediol, and 1,4-butanediol, and a polyhydric alcohol selected from propylene glycol (1,2-propanediol), 1,3-propanediol, and 1,4-butanediol is preferable.

In addition, as the epoxy compound, a polyglycidyl compound is preferable, and ethylene glycol diglycidyl ether is suitably used.

In addition to the above organic surface crosslinking agent, from the viewpoint of more effectively carrying out surface crosslinking, a polyvalent cationic polymer such as a polyamine polymer or a water soluble polyvalent metal cation-containing compound may be used in combination as an ion-binding surface crosslinking agent. The water soluble polyvalent metal cation-containing compound is as described above.

The amount of the surface crosslinking agent used (when a plurality of surface crosslinking agents are used, the total amount thereof used) is preferably 0.01 to 10 parts by weight and more preferably 0.01 to 5 parts by weight per 100 parts by weight of the water-absorbing resin powder. In addition, the surface crosslinking agent is preferably added as an aqueous solution, and in this case, the amount of water used is preferably 0.1 to 20 parts by weight and more preferably 0.5 to 10 parts by weight per 100 parts by weight of the water-absorbing resin powder. Further, when a hydrophilic organic solvent is used as necessary, the amount thereof used is preferably 10 parts by weight or less and more preferably 5 parts by weight or less per 100 parts by weight of the water-absorbing resin powder.

In addition, as described above, a water soluble polyvalent metal cation-containing compound may be added in the surface crosslinking step.

(Mixing Step)

The present step is a step of mixing the water-absorbing resin powder and the surface crosslinking agent. The method for mixing the surface crosslinking agent is not particularly limited, and examples thereof include a method for mixing the surface crosslinking agent by preparing a surface crosslinking agent solution in advance and preferably spraying or dropping, more preferably spraying, the solution onto the water-absorbing resin powder.

The apparatus for carrying out the mixing is not particularly limited, and is preferably a high-speed stirring type mixer, and more preferably a high-speed stirring type continuous mixer.

(Heat Treatment Step)

The present step is a step of applying heat to the mixture discharged from the mixing step to cause a crosslinking reaction on the surface of the water-absorbing resin powder.

The apparatus for carrying out the crosslinking reaction is not particularly limited, and is preferably a paddle dryer. The reaction temperature in the crosslinking reaction is appropriately set according to the type of the surface crosslinking agent used, and is preferably 50 to 300° C. and more preferably 100 to 200° C.

(Cooling Step)

The present step is an optional step provided as necessary after the heat treatment step.

The apparatus for carrying out the cooling is not particularly limited, and is preferably an apparatus having the same specifications as those of the apparatus used in the heat treatment step, and more preferably a paddle dryer. This is because such an apparatus can be used as a cooling apparatus by changing the heat medium to a refrigerant. The water-absorbing resin particle obtained in the heat treatment step are forcibly cooled to 40 to 80° C. and more preferably 50 to 70° C. as necessary, in the cooling step.

(3-7) Additive Addition Step

The present step is a step of adding an additive such as a water soluble polyvalent metal cation-containing compound, a polyvalent metal salt, a cationic polymer, a chelating agent, an inorganic reducing agent, a hydroxycarboxylic acid compound, a water insoluble inorganic particle, a surfactant, or a non-polymer water soluble compound, to the water-absorbing resin particle obtained in the surface crosslinking step. As described above, the additive can also be mixed with the water-absorbing resin powder at the same time as the surface crosslinking agent (aqueous solution).

(Polyvalent Metal Salt and/or Cationic Polymer)

From the viewpoint of improving the water absorption speed, liquid permeability, fluidity after moisture absorption, or the like of the water-absorbing resin obtained, a polyvalent metal salt and/or a cationic polymer may be added.

As the polyvalent metal salt and/or cationic polymer, specifically, the compounds and the amounts thereof used disclosed in "[7] Polyvalent metal salt and/or cationic polymer" of International Publication No. WO 2011/040530 are applied to the present invention.

In particular, as described above, an embodiment in which a water soluble polyvalent metal cation-containing compound is added to the water-absorbing resin particle obtained in the surface crosslinking step is a preferable embodiment because a particulate water-absorbing agent satisfying the expression (1) can be easily obtained.

(Chelating Agent)

A chelating agent may be added from the viewpoint of the color tone (prevention of coloration), prevention of degradation, or the like of the water-absorbing resin obtained.

As the chelating agent, specifically, the compounds and the amounts thereof used disclosed in "[2] Chelating agent" of International Publication No. WO 2011/040530 are applied to the present invention.

(Inorganic Reducing Agent)

An inorganic reducing agent may be added from the viewpoint of the color tone (prevention of coloration) and prevention of degradation of the water-absorbing resin obtained, residual monomer reduction, or the like.

As the inorganic reducing agent, specifically, the compounds and the amounts thereof used disclosed in "[3] Inorganic reducing agent" of International Publication No. WO 2011/040530 are applied to the present invention.

(α-Hydroxycarboxylic Acid Compound)

An α-hydroxycarboxylic acid may be added from the viewpoint of the color tone (prevention of coloration) or the like of the water-absorbing resin obtained. The "α-hydroxycarboxylic acid compound" refers to a carboxylic acid having a hydroxyl group in a molecule or a salt thereof, and is a hydroxycarboxylic acid having a hydroxyl group at the α-position.

As the α-hydroxycarboxylic acid compound, specifically, the compounds and the amounts thereof used disclosed in "[6] α-Hydroxycarboxylic acid compound" of International Publication No. WO 2011/040530 are applied to the present invention.

(Water Insoluble Inorganic Particle)

A water insoluble inorganic particle may be added from the viewpoint of improving the fluidity of the water-absorbing resin or the like. Specific examples thereof include the water insoluble inorganic particles described in the above (2-9) section. As described above, an embodiment in which a water insoluble inorganic particle is added to the water-absorbing resin particle obtained in the surface crosslinking step is a preferable embodiment because a particulate water-absorbing agent satisfying the expression (1) can be easily obtained.

(Surfactant)

A surfactant may be added from the viewpoint of improving a physical property (for example, water absorption speed) of the water-absorbing resin obtained or the like.

Specific examples of the surfactant include the surfactants disclosed in International Publication No. WO 97/017397 and U.S. Pat. No. 6,107,358, that is, a nonionic surfactant, an anionic surfactant, a cationic surfactant, and an amphoteric surfactant.

(Non-Polymer Water Soluble Compound)

A non-polymer water soluble compound may be added from the viewpoint of reducing dust of the water-absorbing resin or the like. The compounds and the amounts thereof used disclosed in "Water-Soluble Non-Polymer Compound" of International Publication No. WO 2014/034667 are applied to the present invention.

In the present invention, additives other than the above additives can also be added in order to impart various functions to the water-absorbing resin. Specific examples of the additives include a compound having a phosphorus atom, an oxidizing agent, an organic reducing agent, an organic powder such as a metal soap, a deodorant, an antibacterial agent, pulp, and a thermoplastic fiber.

The amount of the additives used (amount added) is appropriately determined according to the intended use, thus is not particularly limited, and is preferably 3 parts by weight or less and more preferably 1 part by weight or less per 100 parts by weight of the water-absorbing resin. In addition, the additives can also be added in a step different from the above steps.

(3-8) Other Steps

In the present invention, in addition to the above steps, a granulating step, a sizing step, a fine powder removing step, a fine powder recycling step, or the like can be provided as necessary. In addition, one or two or more steps of a transporting step, a storing step, a packaging step, a reserving step, or the like may be further included. The "sizing step" includes a fine powder removing step after the surface crosslinking step and a step of classifying and pulverizing when the water-absorbing resin aggregates and exceeds a desired size. In addition, the "fine powder recycling step" includes a step of forming a large hydrogel and adding the same to any step of the production steps of the water-absorbing resin, in addition to a formation in which the fine powder is added as it is as in the present invention.

[4] Applications of Particulate Water-Absorbing Agent

The particulate water-absorbing agent of the present invention is used in an application for the purpose of water absorption and is widely used as an absorbent body. In addition, the particulate water-absorbing agent is used as an absorbent article including the absorbent body. In particular, the particulate water-absorbing agent of the present invention is suitably used as a hygiene article for absorbing a body fluid such as urine and blood used by a human among absorbent articles because the wet-back under pressure is reduced.

That is, a suitable embodiment of the present invention is an absorbent body including the particulate water-absorbing agent of the above embodiment.

In addition, another suitable embodiment of the present invention is a hygiene article including the absorbent body of the above embodiment.

Examples of the absorbent body include an absorbing material molded by including a particulate water-absorbing agent and a fiber base material (for example, a hydrophilic fiber) as main components. The content (core concentration) of the particulate water-absorbing agent based on the total weight of the particulate water-absorbing agent and the hydrophilic fiber in the absorbent body is preferably 20 to 100% by weight, more preferably 25 to 90% by weight, and particularly preferably 30 to 80% by weight, and most preferably 40 to 80% by weight. The higher the core concentration in the absorbent body, the more the absorbent body, the absorbent article, or the like is affected by the water absorption performance of the particulate water-absorbing agent during the production thereof. Such an absorbent body is shaped, for example, by blending or sandwiching a fiber base material such as a hydrophilic fiber and the particulate water-absorbing agent. Examples of the fiber base material used include a hydrophilic fiber such as pulverized wood pulp, a cotton linter, a crosslinked cellulose fiber, rayon, cotton, wool, acetate, and vinylon. These fiber base materials are preferably obtained by air-laid.

In addition, the absorbent body may be a water-absorbing sheet (pulpless) in which the water-absorbing resin is immobilized between two sheets (for example, non-woven fabrics).

In addition, the absorbent article is prepared by including the absorbent body, a top sheet having liquid permeability, and a back sheet having no liquid permeability. The absorbent article is made by producing an absorbent body (absorbent core) and sandwiching the absorbent core between a top sheet having liquid permeability and a back sheet having no liquid permeability. Then, the resulting sandwich is provided with an elastic member, a diffusion layer, an adhesive tape, or the like as necessary to obtain an absorbent article such as disposable diapers for an adult or a sanitary napkin. At this time, the absorbent core is compression molded to have, for example, a density in the range of 0.06 to 0.50 [g/cm$^3$] and a basis weight in the range of 0.01 to 0.20 [g/cm$^2$].

EXAMPLES

The present invention will be described in more detail with reference to the following Examples and Comparative Examples. However, the technical scope of the present invention is not limited only to the following Examples. In addition, in the following Examples, unless otherwise specified, the operations were carried out under conditions of room temperature (20 to 25° C.)/a relative humidity of 45 to 55% RH.

Unless otherwise noted, the electrical devices (also including the measurement of physical properties of the particulate water-absorbing agent) used in the Examples, Comparative Examples, and Reference Examples used a power supply of 200 V or 100 V.

(a) Method for Measuring Blocking Ratio (B.R.) after Moisture Absorption 2 g of a particulate water-absorbing agent or a water-absorbing resin was uniformly scattered on an aluminum cup having a diameter of 52 mm and then was allowed to stand for 1 hour in a constant temperature and humidity chamber (PLATINOUS LUCIFER PL-2G; manufactured by Tabai ESPEC Corp.) under a temperature of 25° C. and a relative humidity of 90±5% RH. After 1 hour passed, the particulate water-absorbing agent or water-absorbing resin contained in the aluminum cup was gently transferred onto a JIS standard sieve (The IIDA TESTING SIEVE: inner diameter of 80 mm) having an opening of 2000 μm (JIS 8.6 mesh), and classified for 5 seconds under conditions of room temperature (20 to 25° C.) and a relative humidity of 50% RH using a Ro-tap type sieve shaker (ES-65 type sieve shaker manufactured by SIEVE FACTORY IIDA Co., Ltd.; rotation speed of 230 rpm, number of impacts of 130 rpm). The weight of the particulate water-absorbing agent or water-absorbing resin remaining on the JIS standard sieve (W1 [g]) and the weight of the particulate water-absorbing agent or water-absorbing resin passing through the JIS standard sieve (W2 [g]) were measured, and the fluidity after moisture absorption (blocking ratio after moisture absorption) was calculated according to the following expression. The lower the blocking ratio value, the better the fluidity after moisture absorption.

$$\text{Blocking ratio } (B.R.) \text{ after moisture absorption [\% by weight]} = \{W1/(W1+W2)\}\times 100.$$

(b) Method for Measuring Amount of Dust

The measurement was carried out according to descriptions in [281] to [282] of International Publication No. WO 2006/098271. That is, the amount of dust of the particulate water-absorbing agent was measured by an increase in the weight of the dust sucked and captured by a glass fiber filter paper for a predetermined time under the following conditions. As a measuring apparatus, Heubach DUSTMER manufactured by Heubach Engineering GmbH, Germany, with a measurement mode of Type II was used to carry out the measurement. The temperature of the atmosphere at the time of the measurement was 23° C. (±2° C.), the relative humidity was 20 to 40% RH, and the pressure was normal. The measurement method was as follows.

(1) 100.00 g of a water-absorbing agent as a measurement sample is placed in a rotating drum.

(2) The weight of a glass fiber filter paper having a diameter of 50 mm (for example, manufactured by Advantec MFS, Inc., GLASS FIBER, GC-90 or an equivalent thereof processed to a diameter of 50 mm) and having a retention particle diameter of 0.5 μm (JIS P3801) is measured to the place of 0.00001 g ([Da] g).

(3) A large particle separator is attached to the rotating drum, and a filter case equipped with the glass fiber filter paper is attached.

(4) The measurement conditions of the control unit in the DUSTMETER are set as follows and measurement is carried out. Drum rotation speed: 30 rpm, suction air rate: 4 L/min, Time (measurement time): 30 minutes.

(5) After a predetermined time, the weight of the glass fiber filter paper is measured to the place of 0.00001 g ([Db]).

Using the Da and the Db, the amount of dust is calculated according to the following expression (8).

$$\text{Amount of dust [mg/kg]} = ([Db] - [Da]) / 100 \times 1000000. \quad \text{Expression (8)}$$

(c) Method for Measuring Surface Tension 50 ml of physiological saline adjusted to 20° C. was placed in a 100 ml beaker sufficiently washed, and the surface tension of the physiological saline was first measured using a tensiometer (K11 automatic tensiometer manufactured by KRUSS GmbH). In this measurement, the surface tension value must be in the range of 71 to 75 [mN/m].

Next, in the beaker including the physiological saline adjusted to 20° C. after measuring the surface tension, a 25 mm long fluororesin rotor sufficiently washed and 0.5 g of a particulate water-absorbing agent or a water-absorbing resin were placed and stirred for 4 minutes under a condition of 500 rpm. After 4 minutes, the stirring was stopped, and after the water-containing particulate water-absorbing agent or the water-absorbing resin settled, the surface tension of the supernatant liquid was measured by carrying out the same operation again. In the present invention, a plate method using a platinum plate was adopted, and before each measurement, the plate was sufficiently washed with deionized water and heated and cleaned using a gas burner before use.

(d) Coloration Evaluation (Yellowness/YI Value)

A spectroscopic color difference meter SZ-Σ80COLOR MEASURING SYSTEM manufactured by Nippon Denshoku Industries Co., Ltd. was used for the coloration evaluation of the particulate water-absorbing agent or the water-absorbing resin. Under the set conditions (reflection measurement/attached powder/paste sample stage (inner diameter of 30 mm, height of 12 mm/standard round white plate No. 2 for powder/paste as the standard/30φ projector pipe)), the built-in sample stage was filled with 5 g of the particulate water-absorbing agent or the water-absorbing resin (filling about 60% of the built-in sample stage), and the surface color (YI value (Yellow Index)) was measured using the above spectroscopic color difference meter under conditions of room temperature (20 to 25° C.) and a humidity of 50 RH %. In addition, an object color (L, a, b) or WB (Hunter color) in another scale can be measured at the same time by the same measurement method of the same apparatus. A large L/WB or a smaller a/b indicates that the coloration is less and the color becomes closer to substantially white.

Subsequently, the paste sample stage was filled with 5 g of the particulate water-absorbing agent or the water-absorbing resin, and the paste sample stage filled with the particulate water-absorbing agent or the water-absorbing resin was exposed for 14 days to a constant temperature and humidity chamber (manufactured by ESPEC Corp., product name: Compact Environmental Test Chamber, model SH-641) conditioned to an atmosphere of a temperature of 70±1° C. and a relative humidity of 65±1% RH. After the exposure, the surface color (YI value (Yellow Index)) was measured using the above spectroscopic color difference meter. The YI value is preferably 35 or less, more preferably 32 or less, further preferably 29 or less, and particularly preferably 26 or less.

(e) Paint Shaker Test 30 g of the water-absorbing resin was placed in a glass container having a diameter of 6 cm and a height of 11 cm, and the glass container was installed in a paint shaker (No. 488 test disperser, manufactured by Toyo Seiki Seisaku-sho, Ltd.). Next, the paint shaker was shaken at 800 (cycles/min) for a predetermined time, and then stopped.

Production Example 1

In a polypropylene container having a volume of 2 liters, 351.7 g of acrylic acid, 0.860 g (0.034 mol % based on a carboxyl group-containing unsaturated monomer) of polyethylene glycol diacrylate (molecular weight of 523) as an internal crosslinking agent, 2.15 g of a 1.0% by weight diethylenetriaminepentaacetic acid-trisodium (DTPA·3Na) aqueous solution, 149.0 g of a 48.5% by weight sodium hydroxide aqueous solution, and 336.2 g of deionized water (ion exchanged water) were placed and mixed to prepare a aqueous monomer solution (a').

Next, the aqueous monomer solution (a') was cooled with stirring. When the liquid temperature reached 40.0° C., 144.8 g of a 48.5% by weight sodium hydroxide aqueous solution adjusted to a temperature of 40° C. was added and mixed to prepare a aqueous monomer solution (a). At this time, the temperature of the aqueous monomer solution (a) was raised to 78.2° C. by the heat of the second-stage neutralization immediately after the preparation. Immediately after starting to mix the 48.5% by weight sodium hydroxide aqueous solution, a precipitate was observed, but the precipitate was gradually dissolved and the aqueous monomer solution (a) became a transparent uniform solution.

Next, immediately after adding 15.49 g of a 4.0% by weight sodium persulfate aqueous solution to the above aqueous monomer solution (a) in a stirred state, the resulting mixture was poured into a stainless steel vat type container (bottom surface of 340×340 mm, height of 25 mm, inner surface; Teflon (registered trademark) coating) in a system open to the atmosphere. The time from the start of the second-stage neutralization to the pouring of the aqueous monomer solution (a) into the vat-type container was 55 seconds, and the vat-type container was heated using a hot plate (NEO HOTPLATE HI-1000/Iuchi Seieido Co., Ltd.) until the surface temperature reached 40° C.

A polymerization reaction started 60 seconds after the above aqueous monomer solution (a) was poured into the vat type container. The polymerization reaction proceeded with the aqueous monomer solution (a) expanding and foaming in all directions while generating water vapor, and then the aqueous monomer solution (a) shrank to a size slightly larger than that of the vat type container. 3 Minutes after the start of the polymerization reaction, the crosslinked hydrogel polymer (hereinafter, referred to as the "hydrogel") (1) was taken out. These series of operations were carried out in a system open to the atmosphere.

The hydrogel (1) obtained by the above polymerization reaction was cut into a strip form, supplied to a screw extruder, and subjected to gel-crush to obtain a particulate hydrogel (1). The screw extruder was provided with a perforated plate having a diameter of 100 mm, a hole diameter of 11.0 mm, a number of holes of 40, an aperture ratio of 62.5%, and a thickness of 10 mm at the tip, and the outer diameter of the screw axis was 86 mm.

The above gel-crush was carried out by simultaneously supplying the above hydrogel (1) in a strip form and water vapor from their respective supply ports in a state in which the rotation speed of the screw axis of the screw extruder was 130 rpm. The supply rate of the hydrogel (1) was 4640 g per min, and the supply rate of water vapor was 83 g per min.

This particulate hydrogel (1) was spread out on a 50-mesh wire mesh and dried with hot air at 190° C. for 30 minutes, and the dried product was pulverized using a roll mill (WML type roll crusher/Inoguchi Giken Y.K.), further sieved using JIS standard sieves having openings of 850 μm, 600 μm, 500 μm, 300 μm, and 150 μm, respectively, and then formulated to obtain a precursor water-absorbing resin (A) in an irregularly crushed form having a weight average particle diameter (D50) of 305 μm and a logarithmic standard deviation (σζ) of the particle size distribution of 0.35. The centrifuge retention capacity (CRC) of the precursor water-absorbing resin (A) was 48.4 (g/g).

Production Example 2

In a polypropylene container having a volume of 2 liters, 335.3 g of acrylic acid, 0.720 g (0.030 mol % based on a carboxyl group-containing unsaturated monomer) of polyethylene glycol diacrylate (molecular weight of 523) as an internal crosslinking agent, 2.05 g of a 1.0% by weight diethylenetriaminepentaacetic acid-trisodium (DTPA·3Na) aqueous solution, 142.1 g of a 48.5% by weight sodium hydroxide aqueous solution, and 367.2 g of deionized water (ion exchanged water) were placed and mixed to prepare a aqueous monomer solution (b').

Next, the aqueous monomer solution (b') was cooled with stirring. When the liquid temperature reached 42.0° C., 138.1 g of a 48.5% by weight sodium hydroxide aqueous solution adjusted to a temperature of 40° C. was added and mixed to prepare a aqueous monomer solution (b). At this time, the temperature of the aqueous monomer solution (b) was raised to 77.8° C. by the heat of the second-stage neutralization immediately after the preparation. Immediately after starting to mix the 48.5% by weight sodium hydroxide aqueous solution, a precipitate was observed, but the precipitate was gradually dissolved and the aqueous monomer solution (b) became a transparent uniform solution.

Next, immediately after adding 14.77 g of a 4.0% by weight sodium persulfate aqueous solution to the above aqueous monomer solution (b) in a stirred state, the resulting mixture was poured into a stainless steel vat type container (bottom surface of 340×340 mm, height of 25 mm, inner surface; Teflon (registered trademark) coating) in a system open to the atmosphere. The time from the start of the second-stage neutralization to the pouring of the aqueous monomer solution (b) into the vat-type container was 55 seconds, and the vat-type container was heated using a hot plate (NEO HOTPLATE HI-1000/Iuchi Seieido Co., Ltd.) until the surface temperature reached 40° C.

A polymerization reaction started 60 seconds after the above aqueous monomer solution (b) was poured into the vat type container. The polymerization reaction proceeded with expanding and foaming in all directions while generating water vapor, and then the aqueous monomer solution (b) shrank to a size slightly larger than that of the vat type container. 3 minutes after the start of the polymerization reaction, the crosslinked hydrogel polymer (hereinafter, referred to as the "hydrogel") (2) was taken out. These series of operations were carried out in a system open to the atmosphere.

The hydrogel (2) obtained by the above polymerization reaction was cut into a strip form, supplied to a screw extruder, and subjected to gel-crush to obtain a particulate hydrogel (2). The screw extruder was provided with a perforated plate having a diameter of 100 mm, a hole diameter of 9.5 mm, a number of holes of 40, an aperture ratio of 62.5%, and a thickness of 10 mm at the tip, and the outer diameter of the screw axis was 86 mm.

The above gel-crush was carried out by simultaneously supplying the above hydrogel (2) in a strip form and water vapor from their respective supply ports in a state in which the rotation speed of the screw axis of the screw extruder was 130 rpm. The supply rate of the hydrogel (2) was 4640 g per min, and the supply rate of water vapor was 83 g per min.

This fragmented particulate hydrogel (2) was spread out on a 50-mesh wire mesh and dried with hot air at 190° C. for 30 minutes, and the dried product was pulverized using a roll mill (WML type roll crusher/Inoguchi Giken Y.K.), further sieved using JIS standard sieves having openings of 850 μm, 600 μm, 500 μm, 300 μm, and 150 μm, respectively, and then formulated to obtain a precursor water-absorbing resin (A) in an irregularly crushed form having a weight average particle diameter (D50) of 298 km and a logarithmic standard deviation (σζ) of the particle size distribution of 0.35. The centrifuge retention capacity (CRC) of the precursor water-absorbing resin (B) was 50.1 (g/g).

Example 1-1

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (A) was uniformly mixed and heat-treated at 190° C. for about 30 minutes such that the CRC of the water-absorbing resin (1) obtained was about 35 [g/g]. Then, cooling was carried out, and an aqueous solution consisting of 1 part by weight of deionized water and 0.01 parts by weight of diethylenetriaminepentaacetic acid-trisodium (DTPA·3Na) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: REOLOSIL QS-20, manufactured by Tokuyama Corporation). For the mixing, 30 g of the water-absorbing resin was placed in a mayonnaise bottle having a volume of 225 mL together with silicon dioxide, and these were mixed at 101 rpm for 30 minutes using a Turbula Shaker Mixer T2F type (manufactured by Shinmaru Enterprises Corporation) to obtain a particulate water-absorbing agent (1). The absorption performance of the particulate water-absorbing agent (1) is shown in Table 1. In addition, the AAP4.83 kPa of the particulate water-absorbing agent (1) was 19.4 [g/g], the GPR was 81 [g/min], and the flow rate was 10.1 [g/s].

Example 1-2

A surface crosslinking agent solution consisting of 0.025 parts by weight of ethylene glycol diglycidyl ether, 0.26 parts by weight of 1,3-propanediol, 0.5 parts by weight of propylene glycol, and 2.0 parts by weight of deionized water per 100 parts by weight of the precursor water-absorbing resin (A) was uniformly mixed and heat-treated at 190° C. for about 30 minutes such that the CRC of the water-absorbing resin (2) obtained was about 35 [g/g]. Then, cooling was carried out, and an aqueous solution consisting of 1 part by weight of deionized water and 0.01 parts by weight of ethylenediaminetetramethylenephosphonic acid-pentasodium (EDTMP·5Na) per 100 parts by weight of the water-absorbing resin was uniformly mixed. The resulting mixture was dried 60° C. for 1 hour, then passed through a JIS standard sieve having an opening of 850 μm, and mixed with 0.3 parts by weight of silicon dioxide (trade name: REOLOSIL QS-20, manufactured by Tokuyama Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (2). The absorption performance of the particulate water-absorbing agent (2) is shown in Table 1.

Example 1-3

In Production Example 1, after sieving with JIS standard sieves having openings of 850 μm, 600 μm, 500 μm, 300 μm, and 150 μm, respectively, a surface crosslinking agent solution consisting of 0.025 parts by weight of ethylene glycol diglycidyl ether, 0.31 parts by weight of 1,4-butanediol, 0.5 parts by weight of propylene glycol, and 2.0 parts by weight of deionized water per 100 parts by weight of the precursor water-absorbing resin (A) formulated in such a way as to have a weight average particle diameter (D50) of 343 km and a logarithmic standard deviation ($\sigma\zeta$) of the particle size distribution of 0.36 was uniformly mixed and heat-treated at 190° C. for about 30 minutes such that the water-absorbing resin (3) obtained has a CRC of about 35 [g/g]. Then, cooling was carried out, and an aqueous solution consisting of 1 part by weight of deionized water, 0.03 parts by weight of diethylenetriaminepentaacetic acid-trisodium (DTPA·3Na), and 0.01 parts by weight of polyoxyethylene (20) sorbitan monostearate (trade name: RHEODOL TW-S120V, manufactured by Kao Corporation) per 100 parts by weight of the water-absorbing resin was uniformly mixed. The resulting mixture was dried 60° C. for 1 hour, then passed through a JIS standard sieve having an opening of 850 μm, and mixed with 0.3 parts by weight of silicon dioxide (trade name: AEROSIL 200, manufactured by Nippon Aerosil Co., Ltd.). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (3). The absorption performance of the particulate water-absorbing agent (3) is shown in Table 1.

Example 1-4

A surface crosslinking agent solution consisting of 0.03 parts by weight of ethylene glycol diglycidyl ether, 1.5 parts by weight of propylene glycol, and 3.5 parts by weight of deionized water per 100 parts by weight of the precursor water-absorbing resin (A) was uniformly mixed and heat-treated at 100° C. for about 30 minutes such that the CRC of the water-absorbing resin (4) obtained was about 35 [g/g]. Then, cooling was carried out, and an aqueous solution consisting of 1 part by weight of deionized water and 0.05 parts by weight of diethylenetriaminepentaacetic acid-trisodium (DTPA·3Na) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: REOLOSIL QS-20, manufactured by Tokuyama Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (4). The absorption performance of the particulate water-absorbing agent (4) is shown in Table 1.

Example 1-5

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (A) was uniformly mixed and heat-treated at 190° C. for about 30 minutes such that the CRC of the water-absorbing resin (5) obtained was about 35 [g/g]. Then, cooling was carried out, and an aqueous solution consisting of 1 part by weight of deionized water and 0.01 parts by weight of diethylenetriaminepentaacetic acid-trisodium (DTPA·3Na) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: Sipernat 22S, manufactured by Evonik). For the mixing, 30 g of the water-absorbing resin was placed in a mayonnaise bottle having a volume of 225 mL together with silicon dioxide, and these were mixed at 101 rpm for 45 minutes using a Turbula Shaker Mixer T2F type (manufactured by Shinmaru Enterprises Corporation) to obtain a particulate water-absorbing agent (5). The absorption performance of the particulate water-absorbing agent (5) is shown in Table 1.

Example 1-6

A surface crosslinking agent solution consisting of 0.04 parts by weight of ethylene glycol diglycidyl ether, 2.8 parts by weight of propylene glycol, and 4.2 parts by weight of deionized water per 100 parts by weight of the precursor water-absorbing resin (A) was uniformly mixed and heat-treated at 100° C. for about 30 minutes such that the CRC of the water-absorbing resin (6) obtained was about 35 [g/g]. Then, cooling was carried out, the above paint shaker test (shaking time: 15 minutes) was carried out to apply damage equivalent to that during the production process, and then an aqueous solution consisting of 1 part by weight of deionized water and 0.05 parts by weight of ethylenediaminetetramethylenephosphonic acid-pentasodium (EDTMP·5Na) was uniformly mixed. The resulting mixture was dried at 60° C. for 1 hour, then passed through a JIS standard sieve having an opening of 850 μm, and mixed with 0.3 parts by weight of silicon dioxide (trade name: Sipernat 22S, manufactured by Evonik). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (6). The absorption performance of the particulate water-absorbing agent (6) is shown in Table 1.

Example 1-7

A surface crosslinking agent solution consisting of 0.025 parts by weight of ethylene glycol diglycidyl ether, 0.21 parts by weight of ethylene glycol, 0.5 parts by weight of propylene glycol, and 2.0 parts by weight of deionized water per 100 parts by weight of the precursor water-absorbing resin (A) was uniformly mixed and heat-treated at 190° C. for about 30 minutes such that the CRC of the water-absorbing resin (7) obtained was about 35 [g/g]. Then, cooling was carried out, and an aqueous solution consisting of 0.5 parts by weight of deionized water, 0.05 parts by weight of diethylenetriaminepentaacetic acid-trisodium (DTPA·3Na), and 0.25 parts by weight of polypropylene glycol 700 (manufactured by Kishida Chemical Co., Ltd.) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: OSC C132, Oriental Silicon Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (7). The GPR of the particulate water-absorbing agent (7) was 46 [g/min], and the amount of dust was 70 [mg/kg]. In addition, the absorption performance of the particulate water-absorbing agent (7) is shown in Table 1.

Example 1-8

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (A) was uniformly mixed and heat-treated at 190° C. for about 30 minutes such that the CRC of the water-absorbing resin (8) obtained was about 35 [g/g]. Then, cooling was carried out, and an aqueous solution consisting of 1 part by weight of deionized water, 0.01 parts by weight of diethylenetriaminepentaacetic acid-trisodium (DTPA·3Na), 0.01 parts by weight of polyoxyethylene (20) sorbitan monostearate (trade name: RHEODOL TW-S120V, manufactured by Kao Corporation), and 0.2 parts by weight of polyethylene glycol 400 (trade name: XG-40A, manufactured by Nippon Shokubai Co., Ltd.) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: OSC C132, Oriental Silica Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (8). The absorption performance of the particulate water-absorbing agent (8) is shown in Table 1.

Example 1-9

In Production Example 1, after sieving with JIS standard sieves having openings of 850 μm, 600 μm, 500 μm, 300 μm, and 150 μm, respectively, a surface crosslinking agent solution consisting of 0.03 parts by weight of ethylene glycol diglycidyl ether, 1.2 parts by weight of propylene glycol, and 2.8 parts by weight of deionized water per 100 parts by weight of the precursor water-absorbing resin (A) formulated in such a way as to have a weight average particle diameter (D50) of 379 km and a logarithmic standard deviation (σζ) of the particle size distribution of 0.38 was uniformly mixed and heat-treated at 90° C. for about 30 minutes such that the water-absorbing resin (9) obtained has a CRC of about 35 [g/g]. Then, cooling was carried out, and an aqueous solution consisting of 1 part by weight of deionized water and 0.01 parts by weight of diethylenetriaminepentaacetic acid-trisodium (DTPA·3Na) per 100 parts by weight of the water-absorbing resin was uniformly mixed. The resulting mixture was dried at 60° C. for 1 hour, then passed through a JIS standard sieve having an opening of 850 μm, and mixed with 0.4 parts by weight of aluminum hydroxide (manufactured by FUJIFILM Wako Pure Chemical Corporation). For the mixing, 30 g of the water-absorbing resin was placed in a mayonnaise bottle having a volume of 225 mL together with aluminum hydroxide, and these were mixed at 101 rpm for 60 minutes using a Turbula Shaker Mixer T2F type (manufactured by Shinmaru Enterprises Corporation) to obtain a particulate water-absorbing agent (9). The AAP4.83 kPa of the particulate water-absorbing agent (9) was 22.1 [g/g], and the surface tension was 72.4 mN/m. In addition, the absorption performance of the particulate water-absorbing agent (9) is shown in Table 1.

Example 1-10

A surface crosslinking agent solution consisting of 0.04 parts by weight of ethylene glycol diglycidyl ether, 2.45 parts by weight of propylene glycol, 3.55 parts by weight of deionized water, and 0.75 parts by weight of aluminum sulfate tetradeca- to octadecahydrate per 100 parts by weight of the precursor water-absorbing resin (A) was uniformly mixed and heat-treated at 100° C. for about 30 minutes such that the CRC of the water-absorbing resin (10) obtained was about 35 [g/g]. Then, cooling was carried out, and an aqueous solution consisting of 1 part by weight of deionized water, 0.03 parts by weight of diethylenetriaminepentaacetic acid-trisodium (DTPA·3Na), and 0.1 parts by weight of polypropylene glycol 600 (trade name: PEG-600, manufactured by Sanyo Chemical Industries, Ltd.) per 100 parts by weight of the water-absorbing resin was uniformly mixed.

The resulting mixture was dried at 60° C. for 1 hour and then passed through a JIS standard sieve having an opening of 850 μm. Further, 30 g of the water-absorbing resin was placed in a mayonnaise bottle having a volume of 225 mL and mixed at 101 rpm for 60 minutes using a Turbula Shaker Mixer T2F type (manufactured by Shinmaru Enterprises Corporation) to obtain a particulate water-absorbing agent (10). The AAP4.83 kPa of the particulate water-absorbing agent (10) was 18.5 [g/g], the blocking ratio after moisture absorption was 0 [%], and the amount of dust was 260 [mg/kg]. In addition, the absorption performance of the particulate water-absorbing agent (10) is shown in Table 1.

Example 1-11

A surface crosslinking agent solution consisting of 0.025 parts by weight of ethylene glycol diglycidyl ether, 0.26 parts by weight of 1,3-propanediol, 0.5 parts by weight of propylene glycol, and 2.0 parts by weight of deionized water per 100 parts by weight of the precursor water-absorbing resin (B) was uniformly mixed and heat-treated at 190° C. for about 30 minutes such that the CRC of the water-absorbing resin (11) obtained was about 35 [g/g]. Then, cooling was carried out, and an aqueous solution consisting of 1 part by weight of deionized water and 0.03 parts by weight of diethylenetriaminepentaacetic acid-trisodium (DTPA·3Na) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: REOLOSIL QS-20, manufactured by Tokuyama Corporation). For the mixing, 30 g of the water-absorbing resin was placed in a mayonnaise bottle having a volume of 225 mL together with silicon dioxide, and these were mixed at 101 rpm for 30 minutes using a Turbula Shaker Mixer T2F type (manufactured by Shinmaru Enterprises Corporation) to obtain a particulate water-absorbing agent (11). The absorption performance of the particulate water-absorbing agent (11) is shown in Table 1.

Example 1-12

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (B) was uniformly mixed and heat-treated at 190° C. for about 30 minutes such that the CRC of the water-absorbing resin (12) obtained was about 35 [g/g]. Then, cooling was carried out, and an aqueous solution consisting of 1 part by weight of deionized water, 0.1 parts by weight of ethylenediaminetetramethylenephosphonic acid-pentasodium (EDTMP·5Na), 0.01 parts by weight of polyoxyethylene (20) sorbitan monostearate (trade name: RHEODOL TW-S120V, manufactured by Kao Corporation), and 0.2 parts by weight of polyethylene glycol 1000 (trade name: PEG-1000, manufactured by Sanyo Chemical Industries, Ltd.) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: REOLOSIL QS-20, manufactured by Tokuyama Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (12). The GPR of the particulate water-absorbing agent (12) was 71 [g/min], and the amount of dust was 150 [mg/kg]. In addition, the absorption performance of the particulate water-absorbing agent (12) is shown in Table 1.

Example 1-13

A surface crosslinking agent solution consisting of 0.025 parts by weight of ethylene glycol diglycidyl ether, 0.31 parts by weight of 1,4-butanediol, 0.5 parts by weight of propylene glycol, and 2.0 parts by weight of deionized water per 100 parts by weight of the precursor water-absorbing resin (B) was uniformly mixed and heat-treated at 190° C. for about 30 minutes such that the CRC of the water-absorbing resin (13) obtained was about 35 [g/g]. Then, cooling was carried out, and an aqueous solution consisting of 1 part by weight of deionized water, 0.03 parts by weight of diethylenetriaminepentaacetic acid-trisodium (DTPA·3Na), and 0.1 parts by weight of polypropylene glycol 400 (trade name: XG-40A, manufactured by Nippon Shokubai Co., Ltd.) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: AEROSIL 200, manufactured by Nippon Aerosil Co., Ltd.). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (13). The absorption performance of the particulate water-absorbing agent (13) is shown in Table 1.

Example 1-14

A surface crosslinking agent solution consisting of 0.03 parts by weight of ethylene glycol diglycidyl ether, 1.5 parts by weight of propylene glycol, and 3.5 parts by weight of deionized water per 100 parts by weight of the precursor water-absorbing resin (B) was uniformly mixed and heat-treated at 100° C. for about 30 minutes such that the CRC of the water-absorbing resin (14) obtained was about 35 [g/g]. Then, cooling was carried out, and an aqueous solution consisting of 1 part by weight of deionized water, 0.05 parts by weight of ethylenediaminetetramethylenephosphonic acid-pentasodium (EDTMP·5Na), and 0.05 parts by weight of polypropylene glycol 1000 (trade name: PEG-1000, manufactured by Sanyo Chemical Industries, Ltd.) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: REOLOSIL QS-20, manufactured by Tokuyama Corporation). For the mixing, 30 g of the water-absorbing resin was placed in a mayonnaise bottle having a volume of 225 mL together with silicon dioxide, and these were mixed at 101 rpm for 30 minutes using a Turbula Shaker Mixer T2F type (manufactured by Shinmaru Enterprises Corporation) to obtain a particulate water-absorbing agent (14). The absorption performance of the particulate water-absorbing agent (14) is shown in Table 1.

Example 1-15

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (B) was uniformly mixed and heat-treated at 190° C. for about 30 minutes such that the CRC of the water-absorbing resin (15) obtained was about 35 [g/g]. Then, cooling was carried out, and an aqueous solution consisting of 1 part by weight of deionized water, 0.03 parts by weight of diethylenetriaminepentaacetic acid-trisodium (DTPA·3Na), and 0.01 parts by weight of polyoxyethylene (20) sorbitan monostearate (trade name: RHEODOL TW-S120V, manufactured by Kao Corporation) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: Sipernat 22S, manufactured by Evonik). For the mixing, 30 g of the water-absorbing resin was placed in a mayonnaise bottle having a volume of 225 mL together with silicon dioxide, and these were mixed for 60 minutes using a Turbula Shaker Mixer T2F type (manufactured by Shinmaru Enterprises Corporation) to obtain a particulate water-absorbing agent (15). The absorption performance of the particulate water-absorbing agent (15) is shown in Table 1.

Example 1-16

A surface crosslinking agent solution consisting of 0.04 parts by weight of ethylene glycol diglycidyl ether, 2.8 parts by weight of propylene glycol, and 4.2 parts by weight of deionized water per 100 parts by weight of the precursor water-absorbing resin (B) was uniformly mixed and heat-treated at 100° C. for about 30 minutes such that the CRC of the water-absorbing resin (16) obtained was about 35 [g/g]. Then, cooling was carried out, and an aqueous solution consisting of 1 part by weight of deionized water and 0.01 parts by weight of ethylenediaminetetramethylenephosphonic acid-pentasodium (EDTMP·5Na) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: Sipernat 22S, manufactured by Evonik). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (16). The absorption performance of the particulate water-absorbing agent (16) is shown in Table 1.

Example 1-17

A surface crosslinking agent solution consisting of 0.025 parts by weight of ethylene glycol diglycidyl ether, 0.21 parts by weight of ethylene glycol, 0.5 parts by weight of propylene glycol, and 2.0 parts by weight of deionized water per 100 parts by weight of the precursor water-absorbing resin (B) was uniformly mixed and heat-treated at 190° C. for about 30 minutes such that the CRC of the water-absorbing resin (17) obtained was about 35 [g/g]. Then, cooling was carried out, and an aqueous solution consisting of 1 part by weight of deionized water and 0.05 parts by weight of diethylenetriaminepentaacetic acid-trisodium (DTPA·3Na) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: OSC C132, Oriental Silica Corporation). For the mixing, 30 g of the water-absorbing resin was placed in a mayonnaise bottle having a volume of 225 mL together with silicon dioxide, and these were mixed for 60 minutes using a Turbula Shaker Mixer T2F type (manufactured by Shinmaru Enterprises Corporation) to obtain a particulate water-absorbing agent (17). The absorption performance of the particulate water-absorbing agent (17) is shown in Table 1.

Example 1-18

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (B) was uniformly mixed and heat-treated at 190° C. for about 30 minutes such that the CRC of the water-absorbing resin (18) obtained was about 35 [g/g]. Then, cooling was carried out, and an aqueous solution consisting of 1 part by weight of deionized water, 0.01 parts by weight of diethylenetriaminepentaacetic acid-trisodium (DTPA·3Na), 0.001 parts by weight of polyoxyethylene (20) sorbitan monostearate (trade name: RHEODOL TW-S120V, manufactured by Kao Corporation), and 0.2 parts by weight of polyethylene glycol 600 (trade name: PEG-600, manufactured by Sanyo Chemical Industries, Ltd.) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: OSC C132, Oriental Silica Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (18). The absorption performance of the particulate water-absorbing agent (18) is shown in Table 1.

Example 1-19

A surface crosslinking agent solution consisting of 0.04 parts by weight of ethylene glycol diglycidyl ether, 4.0 parts by weight of propylene glycol, 5.8 parts by weight of deionized water, and 0.75 parts by weight of aluminum sulfate tetradeca- to octadecahydrate (manufactured by FUJIFILM Wako Pure Chemical Corporation) per 100 parts by weight of the precursor water-absorbing resin (A) was uniformly mixed and heat-treated at 100° C. for about 30 minutes such that the CRC of the water-absorbing resin (19) obtained was about 35 [g/g]. Then, cooling was carried out, and an aqueous solution consisting of 1 part by weight of deionized water, 0.05 parts by weight of ethylenediaminetetramethylenephosphonic acid-pentasodium (EDTMP·5Na), and 0.05 parts by weight of polypropylene glycol 700 (manufactured by Kishida Chemical Co., Ltd.) per 100 parts by weight of the water-absorbing resin was uniformly mixed. The resulting mixture was dried at 60° C. for 1 hour and then passed through a JIS standard sieve having an opening of 850 μm. Further, 30 g of the water-absorbing resin was placed in a mayonnaise bottle having a volume of 225 mL and mixed at 101 rpm for 60 minutes using a Turbula Shaker Mixer T2F type (manufactured by Shinmaru Enterprises Corporation) to obtain a particulate water-absorbing agent (19). In addition, the AAP4.83 kPa of the particulate water-absorbing agent (19) was 19.5 [g/g], the GPR was 114 [g/min], and the blocking ratio after moisture absorption was 0 [%]. In addition, the absorption performance of the particulate water-absorbing agent (19) is shown in Table 1.

Example 1-20

In Production Example 1, after sieving with JIS standard sieves having openings of 850 μm, 600 μm, 500 μm, 300 μm, and 150 μm, respectively, a surface crosslinking agent solution consisting of 0.03 parts by weight of ethylene glycol diglycidyl ether, 1.2 parts by weight of propylene glycol, and 2.8 parts by weight of deionized water per 100 parts by weight of the precursor water-absorbing resin (A) formulated in such a way as to have a weight average particle diameter (D50) of 379 km and a logarithmic standard deviation (σζ) of the particle size distribution of 0.38 was uniformly mixed and heat-treated at 90° C. for about 30 minutes such that the water-absorbing resin (20) obtained has a CRC of about 35 [g/g]. Then, cooling was carried out, and an aqueous solution consisting of 1.5 parts by weight of deionized water, 0.01 parts by weight of diethylenetriamine-pentaacetic acid-trisodium (DTPA·3Na), 0.75 parts by weight of aluminum sulfate tetradeca- to octadecahydrate (manufactured by FUJIFILM Wako Pure Chemical Corporation), and 0.75 parts by weight of polypropylene glycol per 100 parts by weight of the water-absorbing resin was uniformly mixed. The resulting mixture was dried at 60° C. for 1 hour and then passed through a JIS standard sieve having an opening of 850 μm. Further, 30 g of the water-absorbing resin was placed in a mayonnaise bottle having a volume of 225 mL and mixed for 60 minutes using a Turbula Shaker Mixer T2F type (manufactured by Shinmaru Enterprises Corporation) to obtain a particulate water-absorbing agent (20). The AAP4.83 kPa of the particulate water-absorbing agent (20) was 22.9 [g/g]. In addition, the absorption performance of the particulate water-absorbing agent (20) is shown in Table 1.

Example 1-21

50 parts by weight of the precursor water-absorbing resin (A) was added to a 99 L plastic bucket filled with deionized water, the resulting mixture was allowed to stand for 10 minutes, and precipitation of the gel was confirmed, and then a mesh sheet having an opening of 150 μm was put on the plastic bucket and fixed to the plastic bucket. A hose was fixed on the mesh sheet, and deionized water was passed through the hose into the plastic bucket for 3 hours. After passing the water, the liquid in the plastic bucket was caused to drain using a JIS standard sieve with an opening of 150 μm, the obtained gel was spread out on a 50-mesh wire mesh, air dried at 60° C. for 24 hours, and then dried under reduced pressure at 60° C. until the moisture content was 7%.

The dried product was pulverized using a roll mill (WML type roll crusher/Inoguchi Giken Y.K.), further sieved using JIS standard sieves having openings of 850 μm, 600 μm, 500 μm, 300 μm, and 150 μm, respectively, and then formulated to obtain a precursor water-absorbing resin (C) in an irregularly crushed form having a weight average particle diameter (D50) of 314 μm and a logarithmic standard deviation (σζ) of the particle size distribution of 0.35. The centrifuge retention capacity (CRC) of the precursor water-absorbing resin (C) was 49.8 (g/g).

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (C) was uniformly mixed and heat-treated at 190° C. for about 30 minutes such that the CRC of the water-absorbing resin (21) obtained was about 35 [g/g]. The absorption performance of the particulate water-absorbing agent (21) is shown in Table 1.

Comparative Example 1-1

A comparative particulate water-absorbing agent (1) was obtained by the same method as in Example 1-1 except that the mixing time of silicon dioxide using a Turbula Shaker Mixer was 2 minutes. The AAP4.83 kPa of the comparative particulate water-absorbing agent (1) was 18.0 [g/g], the GPR was 112 [g/min], and the flow rate was 10.1 [g/s]. In addition, the absorption performance of the comparative particulate water-absorbing agent (1) is shown in Table 1.

Comparative Example 1-2

A comparative particulate water-absorbing agent (2) was obtained by the same method as in Example 1-2 except that the mixing time of silicon dioxide using a Turbula Shaker Mixer was 2 minutes. The absorption performance of the comparative particulate water-absorbing agent (2) is shown in Table 1.

Comparative Example 1-3

A comparative particulate water-absorbing agent (3) was obtained by the same method as in Example 1-4 except that the mixing time of silicon dioxide using a Turbula Shaker Mixer was 2 minutes. The absorption performance of the comparative particulate water-absorbing agent (3) is shown in Table 1.

Comparative Example 1-4

A comparative particulate water-absorbing agent (4) was obtained by the same method as in Example 1-5 except that the mixing time of silicon dioxide using a Turbula Shaker Mixer was 2 minutes. The absorption performance of the comparative particulate water-absorbing agent (4) is shown in Table 1.

Comparative Example 1-5

A comparative particulate water-absorbing agent (5) was obtained by the same method as in Example 1-9 except that 0.4 parts by weight of aluminum hydroxide was changed to 0.3 parts by weight of silicon dioxide (trade name: OSC C132, Oriental Silica Corporation) and the mixing time using a Turbula Shaker Mixer was 2 minutes. The absorption performance of the comparative particulate water-absorbing agent (5) is shown in Table 1. In addition, the surface tension of the comparative particulate water-absorbing agent (5) was 72.3 mN/m.

Comparative Example 1-6

A comparative particulate water-absorbing agent (6) was obtained by the same method as in Example 1-11 except that the mixing time of silicon dioxide using a Turbula Shaker Mixer was 2 minutes. The absorption performance of the comparative particulate water-absorbing agent (6) is shown in Table 1.

Comparative Example 1-7

A comparative particulate water-absorbing agent (7) was obtained by the same method as in Example 1-12 except that the mixing time of silicon dioxide using a Turbula Shaker Mixer was 2 minutes. The absorption performance of the comparative particulate water-absorbing agent (7) is shown in Table 1. In addition, the GPR of the particulate water-absorbing agent (7) was 78 [g/min], and the amount of dust was 160 [mg/kg].

Comparative Example 1-8

A comparative particulate water-absorbing agent (8) was obtained by the same method as in Example 1-13 except that the mixing time of silicon dioxide using a Turbula Shaker Mixer was 2 minutes. The absorption performance of the comparative particulate water-absorbing agent (8) is shown in Table 1.

Comparative Example 1-9

A comparative particulate water-absorbing agent (9) was obtained by the same method as in Example 1-15 except that the mixing time of silicon dioxide using a Turbula Shaker Mixer was 2 minutes. The absorption performance of the comparative particulate water-absorbing agent (9) is shown in Table 1.

Comparative Example 1-10

A comparative particulate water-absorbing agent (10) was obtained by the same method as in Example 1-16 except that the mixing time of silicon dioxide using a Turbula Shaker Mixer was 2 minutes. The absorption performance of the comparative particulate water-absorbing agent (10) is shown in Table 1.

Comparative Example 1-11

A comparative particulate water-absorbing agent (11) was obtained by the same method as in Example 1-17 except that the mixing time of silicon dioxide using a Turbula Shaker Mixer was 2 minutes. The absorption performance of the comparative particulate water-absorbing agent (11) is shown in Table 1.

Comparative Example 1-12

A comparative particulate water-absorbing agent (12) was obtained by the same method as in Example 1-18 except that the mixing time of silicon dioxide using a Turbula Shaker Mixer was 2 minutes. The absorption performance of the comparative particulate water-absorbing agent (12) is shown in Table 1.

Comparative Example 1-13

In Production Example 1, the aqueous monomer solution was adjusted such that the polyethylene glycol diacrylate, which is an internal crosslinking agent, was 0.019 mol % based on the carboxyl group-containing unsaturated monomer, and a precursor water-absorbing resin (D) was obtained by the same method as in Production Example 1. The centrifuge retention capacity (CRC) of the precursor water-absorbing resin (D) was 52.7 (g/g).

A comparative particulate water-absorbing agent (13) was obtained by the same method as in Example 1-4 except that in Examples 1-4, the precursor water-absorbing resin (D) was used, ethylene glycol of the surface crosslinking agent solution was changed to 0.25 parts by weight, the amount of deionized water added to the water-absorbing resin was changed to 10 parts by weight, diethylenetriaminepentaacetic acid-trisodium (DTPA·3Na) was changed to 0.01 parts by weight, silicon dioxide was changed to hydrotalcite (trade name: DHT-6, manufactured by Kyowa Chemical Industry Co., Ltd.), the amount of hydrotalcite mixed was changed to 0.4 parts by weight, and the mixing time using a Turbula Shaker Mixer was changed to 2 minutes. The absorption performance of the comparative particulate water-absorbing agent (13) is shown in Table 1.

Comparative Example 1-14

A comparative particulate water-absorbing agent (14) was obtained by the method of Comparative Example 1-13 except that in Comparative Example 1-13, the amount of deionized water added to the water-absorbing resin was changed to 15 parts by weight, and the type of hydrotalcite was changed (trade name: HT-1-NC, manufactured by Sakai Chemical Industry Co., Ltd.), and the amount of hydrotalcite mixed was changed to 0.2 parts by weight. The absorption performance of the comparative particulate water-absorbing agent (14) is shown in Table 1.

[Evaluation of Absorption Capacity of Absorbent Bodies]

Absorbent bodies A and B were prepared by the methods described below, and the absorption capacity of the absorbent bodies was evaluated.

Method for Preparing Model Absorbent Body A 80 mm×160 mm absorbent cotton (for example, Cut Cotton 8 cm×16 cm manufactured by Kawamoto Corporation can be used) was uniformly torn in the plane direction to prepare two 1.6 g absorbent cotton sheets. Next, a water-absorbing paper was cut out to a size of 200 mm×200 mm, and a frame of 8 cm×16 cm was disposed near the center of the water-absorbing paper. One of the absorbent cotton sheets adjusted to 1.6 g was placed in the frame, the top surface of the absorbent cotton was leveled using an acrylic plate or the like, 3.2 g of the particulate water-absorbing agent was uniformly scattered from the top surface, and further the other of the 1.6 g absorbent cotton sheets was placed thereon to provide a sandwich structure. The absorbent body thus prepared was retained for 1 minute with a load of 10 kg applied to the whole thereof to mold an absorbent body. Then, the load and the frame were removed, and both ends of the absorbent paper were folded back in such a way as to wrap the absorbent body along the longitudinal direction of the absorbent body. This was placed in a non-woven fabric bag (10 cm×22 cm) prepared using Heatron paper, and the periphery thereof was heat-sealed to obtain model absorbent body A.

Method for Preparing Model Absorbent Body B

A 100 mm×180 mm vinyl tape (for example, Vinyl Tape 21-100™ manufactured by Nitto Denko Corporation can be used) was cut out with the adhesive side facing up, a frame of 80 mm×160 mm was disposed in the center thereof, and 3.2 g of the particulate water-absorbing agent was uniformly scattered in the frame. The frame was removed, and a spunbonded non-woven fabric separately cut into a size of 100 mm×180 mm was placed and bonded to the vinyl tape. This was placed in a non-woven fabric bag (10 cm×22 cm) prepared using Heatron paper, and the periphery thereof was heat-sealed to obtain model absorbent body B.

Method for Measuring Absorption Capacity

A 0.9% by weight sodium chloride aqueous solution is placed in a deep vat such that the liquid depth is 5 cm or more, and the temperature of the liquid in the vat is adjusted to 37° C. The model absorbent body was immersed in this vat and swollen for 60 minutes without any load. At the time of the immersion, model absorbent body B was immersed such that the vinyl tape surface faced upward, and all subsequent operations were carried out with the vinyl tape surface facing upward. After swelling, the model absorbent body was taken out from the vat and placed on a JIS standard sieve having a diameter of 45 cm and an opening of 2000 μm, and a weight of 2690 g was placed on an area of 8 cm×16 cm in which the particulate water-absorbing agent of the model absorbent body was present (21 g/cm$^2$), to carry out draining for 1 minute. The weight of the model absorbent body after draining was measured, and the difference thereof from the weight of the model absorbent body before immersion measured in advance was taken as the absorption capacity. The results are shown in Table 1.

TABLE 1

| | Precursor water-absorbing resin | Additive | Mixing time [min] | CRC [g/g] | AAP2.06 kPa [g/g] |
|---|---|---|---|---|---|
| Example 1-1 | Precursor water-absorbing resin (A) | (1) | 30 | 34.8 | 30.9 |
| Example 1-2 | Precursor water-absorbing resin (A) | (1) | 60 | 35.4 | 30.2 |
| Example 1-3 | Precursor water-absorbing resin (A) | (2) | 60 | 34.5 | 31.0 |
| Example 1-4 | Precursor water-absorbing resin (A) | (1) | 60 | 35.0 | 29.4 |
| Example 1-5 | Precursor water-absorbing resin (A) | (3) | 45 | 35.5 | 32.0 |
| Example 1-6 | Precursor water-absorbing resin (A) | (3) | 60 | 33.5 | 31.5 |
| Example 1-7 | Precursor water-absorbing resin (A) | (4) | 60 | 34.2 | 32.1 |
| Example 1-8 | Precursor water-absorbing resin (A) | (4) | 60 | 34.6 | 32.2 |
| Example 1-9 | Precursor water-absorbing resin (A) | Aluminum hydroxide | 60 | 33.8 | 30.2 |
| Example 1-10 | Precursor water-absorbing resin (A) | Aluminum sulfate | 60 | 35.7 | 30.6 |
| Example 1-11 | Precursor water-absorbing resin (B) | (1) | 30 | 35.9 | 30.7 |
| Example 1-12 | Precursor water-absorbing resin (B) | (1) | 60 | 36.2 | 31.2 |
| Example 1-13 | Precursor water-absorbing resin (B) | (2) | 60 | 36.5 | 31.3 |
| Example 1-14 | Precursor water-absorbing resin (B) | (1) | 30 | 36.8 | 30.4 |
| Example 1-15 | Precursor water-absorbing resin (B) | (3) | 60 | 33.3 | 31.4 |
| Example 1-16 | Precursor water-absorbing resin (B) | (3) | 60 | 35.3 | 31.7 |
| Example 1-17 | Precursor water-absorbing resin (B) | (4) | 60 | 35.1 | 32 |
| Example 1-18 | Precursor water-absorbing resin (B) | (4) | 60 | 33.3 | 31.7 |
| Example 1-19 | Precursor water-absorbing resin (A) | Aluminum sulfate (aqueous solution) | 60 | 32.9 | 30.0 |
| Example 1-20 | Precursor water-absorbing resin (A) | Aluminum sulfate (aqueous solution) | 60 | 33.7 | 30.1 |
| Example 1-21 | Precursor water-absorbing resin (C) | — | — | 37.6 | 31.2 |
| Comparative Example 1-1 | Precursor water-absorbing resin (A) | (1) | 2 | 34.5 | 29.8 |
| Comparative Example 1-2 | Precursor water-absorbing resin (A) | (1) | 2 | 35.0 | 29.5 |
| Comparative Example 1-3 | Precursor water-absorbing resin (A) | (1) | 2 | 35.1 | 28.5 |
| Comparative Example 1-4 | Precursor water-absorbing resin (A) | (3) | 2 | 35.3 | 30.7 |
| Comparative Example 1-5 | Precursor water-absorbing resin (A) | (4) | 2 | 33.6 | 29.1 |
| Comparative Example 1-6 | Precursor water-absorbing resin (B) | (1) | 2 | 35.7 | 29.4 |
| Comparative Example 1-7 | Precursor water-absorbing resin (B) | (1) | 2 | 36.4 | 29.9 |
| Comparative Example 1-8 | Precursor water-absorbing resin (B) | (2) | 2 | 36.3 | 30.1 |
| Comparative Example 1-9 | Precursor water-absorbing resin (B) | (3) | 2 | 33.5 | 30.2 |
| Comparative Example 1-10 | Precursor water-absorbing resin (B) | (3) | 2 | 35.5 | 30.6 |
| Comparative Example 1-11 | Precursor water-absorbing resin (B) | (4) | 2 | 35.0 | 30.8 |
| Comparative Example 1-12 | Precursor water-absorbing resin (B) | (4) | 2 | 33.6 | 30.5 |
| Comparative Example 1-13 | Precursor water-absorbing resin (D) | (5) | 2 | 36.3 | 28.7 |
| Comparative Example 1-14 | Precursor water-absorbing resin (D) | (6) | 2 | 33.4 | 27.7 |

TABLE 1-continued

| | RCAP2.06 kPa [g/g] | AAP2.06 kPa + RCAP2.06 kPa [g/g] | Evaluation of absorbent body A used for diapers (Absorbent body A) Absorption capacity (g) | Evaluation of absorbent body B used for diapers (Absorbent body B) Absorption capacity (g) |
|---|---|---|---|---|
| Example 1-1 | 46.4 | 77.3 | 144 | 121 |
| Example 1-2 | 46.8 | 77.0 | 143 | 120 |
| Example 1-3 | 46 | 77.0 | 140 or more | 119 or more |
| Example 1-4 | 46.8 | 76.2 | 141 | 118 |
| Example 1-5 | 46.5 | 78.5 | 146 | 122 |
| Example 1-6 | 46 | 77.5 | 140 or more | 119 or more |
| Example 1-7 | 45.8 | 77.9 | 140 or more | 119 or more |
| Example 1-8 | 45.4 | 77.6 | 140 or more | 119 or more |
| Example 1-9 | 47.6 | 77.8 | 147 | 123 |
| Example 1-10 | 48.3 | 78.9 | 140 or more | 119 or more |
| Example 1-11 | 46.1 | 76.8 | 142 | 119 |
| Example 1-12 | 45.8 | 77.0 | 142 | 120 |
| Example 1-13 | 46.9 | 78.2 | 148 | 122 |
| Example 1-14 | 46.9 | 77.3 | 140 or more | 119 or more |
| Example 1-15 | 45.3 | 76.7 | 144 | 120 |
| Example 1-16 | 46.0 | 77.7 | 147 | 121 |
| Example 1-17 | 45.0 | 77.0 | 145 | 122 |
| Example 1-18 | 44.9 | 76.6 | 144 | 121 |
| Example 1-19 | 46.1 | 76.1 | 145 | 119 |
| Example 1-20 | 46.0 | 76.1 | 140 or more | 119 or more |
| Example 1-21 | 48.1 | 79.3 | 140 or more | 119 or more |
| Comparative Example 1-1 | 45.1 | 74.9 | 139 | 115 |
| Comparative Example 1-2 | 44.8 | 74.3 | 138 | 114 |
| Comparative Example 1-3 | 44.3 | 72.8 | 136 | 111 |
| Comparative Example 1-4 | 44.5 | 75.2 | 139 | 115 |
| Comparative Example 1-5 | 45.5 | 74.6 | 139 | 115 |
| Comparative Example 1-6 | 45 | 74.4 | 136 | 113 |
| Comparative Example 1-7 | 44.5 | 74.4 | 138 | 114 |
| Comparative Example 1-8 | 45.5 | 75.6 | 139 | 116 |
| Comparative Example 1-9 | 44.3 | 74.5 | 137 | 114 |
| Comparative Example 1-10 | 44.7 | 75.3 | 138 | 116 |
| Comparative Example 1-11 | 43.8 | 74.6 | 138 | 114 |
| Comparative Example 1-12 | 43.4 | 73.9 | 136 | 114 |
| Comparative Example 1-13 | 42.2 | 70.9 | less than 140 | 117 or less |
| Comparative Example 1-14 | 41.0 | 68.7 | less than 140 | 117 or less |

(Note)
Additive column (1) silicon dioxide (REOLOSIL QS-20),
(2) silicon dioxide (AEROSIL 200),
(3) silicon dioxide (Sipernat 22S),
(4) silicon dioxide (OSC C132),
(5) hydrotalcite (DHT-6),
(6) hydrotalcite (HT-1-NC)

Figure 2:
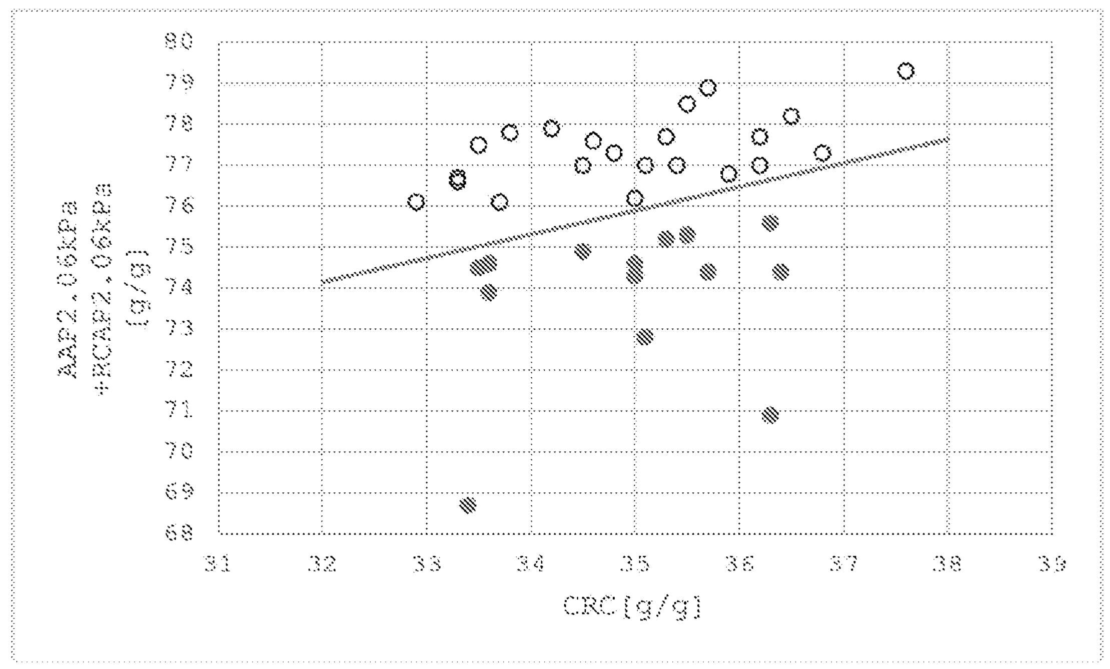
FIG. 2 is a diagram plotting AAP (2.06 kPa)+RCAP (2.06 kPa) [g/g] (vertical axis) versus CRC [g/g] (horizontal axis) in each Example and Comparative Example. The straight line represents AAP (2.06 kPa)+RCAP (2.06 kPa)=0.58×CRC+55.6.

FIG. 2 is a diagram plotting AAP (2.06 kPa)+RCAP (2.06 kPa) [g/g] (vertical axis) versus CRC [g/g](horizontal axis) for the above Examples and Comparative Examples. The straight line represents AAP (2.06 kPa)+RCAP (2.06 kPa)=0.58×CRC+55.6.

As can be seen from the evaluation results of the absorbent bodies in Table 1, each of the particulate water-absorbing agents of the Examples, which is a particulate water-absorbing agent satisfying the expression (1), had a higher liquid retention capacity (absorption capacity) under pressure by 1 g or more even in a state in which the particulate water absorbent absorbed the liquid and swelled, when used as an absorbent body, than those of the Comparative Examples. This difference in the liquid capacity is a remarkable difference in the art. From this result, it can be seen that each of the particulate water-absorbing agents of the Examples can significantly reduce the re-wet even if pressure is applied to the particulate water-absorbing agent from the outside when the particulate water-absorbing agent is in a swollen state.

Production Example 3

In a polypropylene container having a volume of 2 liters, 351.7 g of acrylic acid, 0.910 g (0.036 mol % based on a carboxyl group-containing unsaturated monomer) of polyethylene glycol diacrylate (molecular weight of 523) as an internal crosslinking agent, 2.15 g of a 1.0% by weight diethylenetriaminepentaacetic acid-trisodium (DTPA·3Na) aqueous solution, 149.0 g of a 48.5% by weight sodium hydroxide aqueous solution, 1.41 g (malic acid is 0.108 mol % based on a carboxyl group-containing unsaturated monomer) of a 50.0% by weight malic acid aqueous solution (DL-malic acid, 50.0% aqueous solution, manufactured by Fuso Chemical Co., Ltd., food additive grade), and 336.2 g of deionized water (ion exchanged water) were placed and mixed to prepare a aqueous monomer solution (e').

Next, the aqueous monomer solution (e') was cooled with stirring. When the liquid temperature reached 40.0° C., 144.8 g of a 48.5% by weight sodium hydroxide aqueous solution adjusted to a temperature of 40° C. was added and mixed to prepare a aqueous monomer solution (e). At this time, the temperature of the aqueous monomer solution (e) was raised to 77.9° C. by the heat of the second-stage neutralization immediately after the preparation. Immediately after starting to mix the 48.5% by weight sodium hydroxide aqueous solution, a precipitate was observed, but the precipitate was gradually dissolved and the aqueous monomer solution (e) became a transparent uniform solution.

Next, immediately after adding 15.49 g of a 4.0% by weight sodium persulfate aqueous solution to the above aqueous monomer solution (e) in a stirred state, the resulting mixture was poured into a stainless steel vat type container (bottom surface of 340×340 mm, height of 25 mm, inner surface; Teflon (registered trademark) coating) in a system open to the atmosphere. The time from the start of the second-stage neutralization to the pouring of the aqueous monomer solution (e) into the vat-type container was 55 seconds, and the vat-type container was heated using a hot plate (NEO HOTPLATE HI-1000/Iuchi Seieido Co., Ltd.) until the surface temperature reached 40° C.

A polymerization reaction started 60 seconds after the above aqueous monomer solution (e) was poured into the vat type container. The polymerization reaction proceeded with the aqueous monomer solution (e) expanding and foaming in all directions while generating water vapor, and then the aqueous monomer solution (e) shrank to a size slightly larger than that of the vat type container. 3 Minutes after the start of the polymerization reaction, the crosslinked hydrogel polymer (hereinafter, referred to as the "hydrogel") (3) was taken out. These series of operations were carried out in a system open to the atmosphere.

The hydrogel (3) obtained by the above polymerization reaction was cut into a strip form, supplied to a screw extruder, and subjected to gel-crush to obtain a particulate hydrogel (3). The screw extruder was provided with a perforated plate having a diameter of 100 mm, a hole diameter of 11.0 mm, a number of holes of 40, an aperture ratio of 62.5%, and a thickness of 10 mm at the tip, and the outer diameter of the screw axis was 86 mm.

The above gel-crush was carried out by simultaneously supplying the above hydrogel (3) in a strip form and water vapor from their respective supply ports in a state in which the rotation speed of the screw axis of the screw extruder was 130 rpm. The supply rate of the hydrogel (3) was 4640 g per min, and the supply rate of water vapor was 83 g per min.

This particulate hydrogel (3) was spread out on a 50-mesh wire mesh and dried with hot air at 190° C. for 30 minutes, and the dried product was pulverized using a roll mill (WML type roll crusher/Inoguchi Giken Y.K.), further sieved using JIS standard sieves having openings of 850 μm, 600 μm, 500 μm, 300 μm, and 150 μm, respectively, and then formulated to obtain a precursor water-absorbing resin (E) in an irregularly crushed form having a weight average particle diameter (D50) of 303 μm and a logarithmic standard deviation (σζ) of the particle size distribution of 0.36. The centrifuge retention capacity (CRC) of the precursor water-absorbing resin (E) was 50.2 (g/g).

Production Example 4

In a polypropylene container having a volume of 2 liters, 335.3 g of acrylic acid, 1.344 g (0.056 mol % based on a carboxyl group-containing unsaturated monomer) of polyethylene glycol diacrylate (molecular weight of 523) as an internal crosslinking agent, 2.05 g of a 1.0% by weight diethylenetriaminepentaacetic acid-trisodium (DTPA·3Na) aqueous solution, 142.1 g of a 48.5% by weight sodium hydroxide aqueous solution, 6.706 g (malic acid is 0.537 mol % based on a carboxyl group-containing unsaturated monomer) of a 50.0% by weight malic acid aqueous solution (DL-malic acid, 50.0% aqueous solution, manufactured by Fuso Chemical Co., Ltd., food additive grade), and 367.2 g of deionized water (ion exchanged water) were placed and mixed to prepare a aqueous monomer solution (f').

Next, the aqueous monomer solution (f') was cooled with stirring. When the liquid temperature reached 42.0° C., 138.1 g of a 48.5% by weight sodium hydroxide aqueous solution adjusted to a temperature of 40° C. was added and mixed to prepare a aqueous monomer solution (f). At this time, the temperature of the aqueous monomer solution (f) was raised to 78.1° C. by the heat of the second-stage neutralization immediately after the preparation. Immediately after starting to mix the 48.5% by weight sodium hydroxide aqueous solution, a precipitate was observed, but the precipitate was gradually dissolved and the aqueous monomer solution (f) became a transparent uniform solution.

Next, immediately after adding 14.77 g of a 4.0% by weight sodium persulfate aqueous solution to the above aqueous monomer solution (f) in a stirred state, the resulting mixture was poured into a stainless steel vat type container (bottom surface of 340×340 mm, height of 25 mm, inner surface; Teflon (registered trademark) coating) in a system open to the atmosphere. The time from the start of the second-stage neutralization to the pouring of the aqueous monomer solution (f) into the vat-type container was 55 seconds, and the vat-type container was heated using a hot plate (NEO HOTPLATE HI-1000/Iuchi Seieido Co., Ltd.) until the surface temperature reached 40° C.

A polymerization reaction started 60 seconds after the above aqueous monomer solution (f) was poured into the vat type container. The polymerization reaction proceeded with the aqueous monomer solution (f) expanding and foaming in all directions while generating water vapor, and then the aqueous monomer solution (f) shrank to a size slightly larger than that of the vat type container. 3 Minutes after the start of the polymerization reaction, the crosslinked hydrogel polymer (hereinafter, referred to as the "hydrogel") (4) was taken out. These series of operations were carried out in a system open to the atmosphere.

The hydrogel (4) obtained by the above polymerization reaction was cut into a strip form, supplied to a screw extruder, and subjected to gel-crush to obtain a particulate hydrogel (4). The screw extruder was provided with a perforated plate having a diameter of 100 mm, a hole diameter of 9.5 mm, a number of holes of 40, an aperture ratio of 62.5%, and a thickness of 10 mm at the tip, and the outer diameter of the screw axis was 86 mm.

The above gel-crush was carried out by simultaneously supplying the above hydrogel (4) in a strip form and water vapor from their respective supply ports in a state in which the rotation speed of the screw axis of the screw extruder was 130 rpm. The supply rate of the hydrogel (4) was 4640 g per min, and the supply rate of water vapor was 83 g per min.

This fragmented particulate hydrogel (4) was spread out on a 50-mesh wire mesh and dried with hot air at 190° C. for 30 minutes, and the dried product was pulverized using a roll mill (WML type roll crusher/Inoguchi Giken Y.K.), further sieved using JIS standard sieves having openings of 850 μm, 600 μm, 500 μm, 300 μm, and 150 μm, respectively, and then formulated to obtain a precursor water-absorbing resin (F) in an irregularly crushed form having a weight average particle diameter (D50) of 303 km and a logarithmic standard deviation (σζ) of the particle size distribution of 0.35. The centrifuge retention capacity (CRC) of the precursor water-absorbing resin (F) was 49.6 (g/g).

Example 2-1

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (E) was uniformly mixed and heat-treated at 190° C. for about 30 minutes such that the CRC of the water-absorbing resin (22) obtained was about 35 [g/g]. Then, cooling was carried out, and an aqueous solution consisting of 1 part by weight of deionized water, 0.05 parts by weight of ethylenediaminetetramethylenephosphonic acid-pentasodium (EDTMP·5Na), and 0.15 parts by weight of sodium sulfite per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: REOLOSIL QS-20, manufactured by Tokuyama Corporation). For the mixing, 30 g of the water-absorbing resin was placed in a mayonnaise bottle having a volume of 225 mL together with silicon dioxide, and these were mixed at 101 rpm for 30 minutes using a Turbula Shaker Mixer T2F type (manufactured by Shinmaru Enterprises Corporation) to obtain a particulate water-absorbing agent (22). The GPR of the particulate water-absorbing agent (22) was 84 [g/min], the surface tension was 72.3 mN/m, and the YI value after coloration evaluation was 24. The absorption performance of the particulate water-absorbing agent (22) is shown in Table 2.

Example 2-2

A surface crosslinking agent solution consisting of 0.025 parts by weight of ethylene glycol diglycidyl ether, 0.21 parts by weight of ethylene glycol, 0.5 parts by weight of propylene glycol, and 2.0 parts by weight of deionized water per 100 parts by weight of the precursor water-absorbing resin (E) was uniformly mixed and heat-treated at 190° C. for about 30 minutes such that the CRC of the water-absorbing resin (23) obtained was about 35 [g/g]. Then, cooling was carried out, and an aqueous solution consisting of 1 part by weight of deionized water and 0.03 parts by weight of diethylenetriaminepentaacetic acid-trisodium (DTPA·3Na) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: OSC C132, Oriental Silicon Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (23). The absorption performance of the particulate water-absorbing agent (23) is shown in Table 2.

Example 2-3

A surface crosslinking agent solution consisting of 0.025 parts by weight of ethylene glycol diglycidyl ether, 1.2 parts by weight of propylene glycol, and 2.8 parts by weight of deionized water per 100 parts by weight of the precursor water-absorbing resin (E) was uniformly mixed and heat-treated at 100° C. for about 30 minutes such that the CRC of the water-absorbing resin (24) obtained was about 35 [g/g]. Then, cooling was carried out, the above paint shaker test (shaking time: 10 minutes) was carried out to apply damage equivalent to that during the production process, and then an aqueous solution consisting of 1 part by weight of deionized water, 0.02 parts by weight of diethylenetriaminepentaacetic acid-trisodium (DTPA·3Na), and 0.2 parts by weight of polyethylene glycol 600 (trade name: PEG-600, manufactured by Sanyo Chemical Industries, Ltd.) was uniformly mixed. The resulting mixture was dried at 60° C. for 1 hour, then passed through a JIS standard sieve having an opening of 850 μm, and mixed with 0.3 parts by weight of silicon dioxide (trade name: Sipernat 22S, manufactured by Evonik). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (24). The absorption performance of the particulate water-absorbing agent (24) is shown in Table 2.

Example 2-4

A surface crosslinking agent solution consisting of 0.04 parts by weight of ethylene glycol diglycidyl ether, 3.5 parts by weight of propylene glycol, 5.0 parts by weight of deionized water, and 0.75 parts by weight of aluminum sulfate tetradeca- to octadecahydrate per 100 parts by weight of the precursor water-absorbing resin (E) was uniformly mixed and heat-treated at 100° C. for about 30 minutes such that the CRC of the water-absorbing resin (25) obtained was about 35 [g/g]. Then, cooling was carried out, and an aqueous solution consisting of 1 part by weight of deionized water, 0.01 parts by weight of diethylenetriaminepentaacetic acid-trisodium (DTPA·3Na), and 0.05 parts by weight of polypropylene glycol 700 (manufactured by Kishida Chemical Co., Ltd.) per 100 parts by weight of the water-absorbing resin was uniformly mixed. The resulting mixture was dried at 60° C. for 1 hour and then passed through a JIS standard sieve having an opening of 850 μm. Further, 30 g of the water-absorbing resin was placed in a mayonnaise bottle having a volume of 225 mL and mixed at 101 rpm for 60 minutes using a Turbula Shaker Mixer T2F type (manufactured by Shinmaru Enterprises Corporation) to obtain a particulate water-absorbing agent (25). The AAP4.83 kPa of the particulate water-absorbing agent (25) was 19.1 [g/g], the GPR was 79 [g/min], and the blocking ratio after moisture absorption was 0 [%]. The absorption performance of the particulate water-absorbing agent (25) is shown in Table 2.

Example 2-5

A surface crosslinking agent solution consisting of 0.025 parts by weight of ethylene glycol diglycidyl ether, 0.3 parts by weight of ethylene carbonate, 0.5 parts by weight of propylene glycol, and 2.0 parts by weight of deionized water per 100 parts by weight of the precursor water-absorbing resin (F) was uniformly mixed and heat-treated at 190° C. for about 30 minutes such that the CRC of the water-absorbing resin (26) obtained was about 35 [g/g]. Then, cooling was carried out, and an aqueous solution consisting of 1 part by weight of deionized water, 0.1 parts by weight of ethylenediaminetetramethylenephosphonic acid-pentasodium (EDTMP·5Na), 0.01 parts by weight of polyoxyethylene (20) sorbitan monostearate (trade name: RHEODOL TW-S120V, manufactured by Kao Corporation), and 0.2 parts by weight of polyethylene glycol 1000 (trade name: PEG-1000, manufactured by Sanyo Chemical Industries, Ltd.) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: OSC C132, Oriental Silicon Corporation). For the mixing, 30 g of the water-absorbing resin was placed in a mayonnaise bottle having a volume of 225 mL together with silicon dioxide, and these were mixed at 101 rpm for 60 minutes using a Turbula Shaker Mixer T2F type (manufactured by Shinmaru Enterprises Corporation) to obtain a particulate water-absorbing agent (26). The absorption performance of the particulate water-absorbing agent (26) is shown in Table 2.

Example 2-6

A surface crosslinking agent solution consisting of 0.04 parts by weight of ethylene glycol diglycidyl ether, 2.8 parts by weight of propylene glycol, and 4.2 parts by weight of deionized water per 100 parts by weight of the precursor water-absorbing resin (F) was uniformly mixed and heat-treated at 100° C. for about 30 minutes such that the CRC of the water-absorbing resin (27) obtained was about 35 [g/g]. Then, cooling was carried out, and an aqueous solution consisting of 1 part by weight of deionized water, 0.03 parts by weight of diethylenetriaminepentaacetic acid-trisodium (DTPA·3Na), and 0.01 parts by weight of polyoxyethylene (20) sorbitan monostearate (trade name: RHEODOL TW-S120V, manufactured by Kao Corporation) per 100 parts by weight of the water-absorbing resin was uniformly mixed. The resulting mixture was dried at 60° C. for 1 hour, then passed through a JIS standard sieve having an opening of 850 μm, and mixed with 0.3 parts by weight of silicon dioxide (trade name: Sipernat 22S, manufactured by Evonik). For the mixing, 30 g of the water-absorbing resin was placed in a mayonnaise bottle having a volume of 225 mL together with silicon dioxide, and these were mixed at 101 rpm for 45 minutes using a Turbula Shaker Mixer T2F type (manufactured by Shinmaru Enterprises Corporation) to obtain a particulate water-absorbing agent (27). The flow rate of the particulate water-absorbing agent (27) was 9.4 [g/s], and the YI value after coloration evaluation was 23. The absorption performance of the particulate water-absorbing agent (27) is shown in Table 2.

Example 2-7

A surface crosslinking agent solution consisting of 0.03 parts by weight of ethylene glycol diglycidyl ether, 1.5 parts by weight of propylene glycol, and 3.5 parts by weight of deionized water per 100 parts by weight of the precursor water-absorbing resin (F) was uniformly mixed and heat-treated at 100° C. for about 30 minutes such that the CRC of the water-absorbing resin (28) obtained was about 35 [g/g]. Then, cooling was carried out, and an aqueous solution consisting of 1 part by weight of deionized water, 0.01 parts by weight of ethylenediaminetetramethylenephosphonic acid-pentasodium (EDTMP·5Na), and 0.1 parts by weight of sodium hydrogen sulfite per 100 parts by weight of the water-absorbing resin was uniformly mixed. The resulting mixture was dried at 60° C. for 1 hour, then passed through a JIS standard sieve having an opening of 850 μm, and mixed with 0.4 parts by weight of aluminum hydroxide (manufactured by FUJIFILM Wako Pure Chemical Corporation). For the mixing, 30 g of the water-absorbing resin was placed in a mayonnaise bottle having a volume of 225 mL together with aluminum hydroxide, and these were mixed at 101 rpm for 60 minutes using a Turbula Shaker Mixer T2F type (manufactured by Shinmaru Enterprises Corporation) to obtain a particulate water-absorbing agent (28). The absorption performance of the particulate water-absorbing agent (28) is shown in Table 2.

Example 2-8

A surface crosslinking agent solution consisting of 0.04 parts by weight of ethylene glycol diglycidyl ether, 2.8 parts by weight of propylene glycol, 4.2 parts by weight of deionized water, and 0.75 parts by weight of aluminum sulfate tetradeca- to octadecahydrate (manufactured by FUJIFILM Wako Pure Chemical Corporation) per 100 parts by weight of the precursor water-absorbing resin (F) was uniformly mixed and heat-treated at 100° C. for about 30 minutes such that the CRC of the water-absorbing resin (29) obtained was about 35 [g/g]. Then, cooling was carried out, and an aqueous solution consisting of 1 part by weight of deionized water, 0.05 parts by weight of diethylenetriaminepentaacetic acid-trisodium (DTPA·3Na), 0.3 parts by weight of polypropylene glycol 400 (trade name: XG-40A, manufactured by Nippon Shokubai Co., Ltd.), and 0.03 parts by weight of sodium sulfite per 100 parts by weight of the water-absorbing resin was uniformly mixed. The resulting mixture was dried at 60° C. for 1 hour and then passed through a JIS standard sieve having an opening of 850 μm. Further, 30 g of the water-absorbing resin was placed in a mayonnaise bottle having a volume of 225 mL and mixed at 101 rpm for 60 minutes using a Turbula Shaker Mixer T2F type (manufactured by Shinmaru Enterprises Corporation) to obtain a particulate water-absorbing agent (29). The amount of dust of the particulate water-absorbing agent (29) was 50 [mg/kg], and the YI value after coloration evaluation was 25. The absorption performance of the particulate water-absorbing agent (29) is shown in Table 2.

Example 2-9

A particulate water-absorbing agent (30) was obtained by the same method as in Example 2-1 except that the mixing time of silicon dioxide using a Turbula Shaker Mixer was 15 minutes. The water absorption performance of the particulate water-absorbing agent (30) is shown in Table 2.

Comparative Example 2-1

A comparative particulate water-absorbing agent (15) was obtained by the same method as in Example 2-1 except that the mixing time of silicon dioxide using a Turbula Shaker Mixer was 2 minutes. The GPR of the comparative particulate water-absorbing agent (15) was 100 [g/min], the surface tension was 72.2 mN/m, and the YI value after coloration evaluation was 24. The absorption performance of the comparative particulate water-absorbing agent (15) is shown in Table 2.

Comparative Example 2-2

A comparative particulate water-absorbing agent (16) was obtained by the same method as in Example 2-3 except that the mixing time of silicon dioxide using a Turbula Shaker Mixer was 2 minutes. The absorption performance of the comparative particulate water-absorbing agent (16) is shown in Table 2.

Comparative Example 2-3

A comparative particulate water-absorbing agent (17) was obtained by the same method as in Example 2-5 except that the mixing time of silicon dioxide using a Turbula Shaker Mixer was 2 minutes. The absorption performance of the comparative particulate water-absorbing agent (17) is shown in Table 2.

Comparative Example 2-4

A comparative particulate water-absorbing agent (18) was obtained by the same method as in Example 2-6 except that the mixing time of silicon dioxide using a Turbula Shaker Mixer was 2 minutes. The flow rate of the comparative particulate water-absorbing agent (18) was 9.2 [g/s], and the YI value after coloration evaluation was 23. In addition, the absorption performance of the comparative particulate water-absorbing agent (18) is shown in Table 2.

Comparative Example 2-5

A polyethylene bag with a zipper (size inside the zipper: 70 mm×50 mm, thickness of 0.04 mm, volume of 35 mL) was filled with 25.5 g of a particulate water-absorbing agent (in an irregularly crushed form) collected by removing pulp as much as possible from the absorbent body of diapers manufactured by Daio Paper Corporation “GOO.N Pants Massara Sara Breathable for Boys L Size” (purchased in 2020). This polyethylene bag was placed on a JIS standard sieve having an opening of 850 mm and an inner diameter of 200 mm. The standard sieve was fixed to a sieve shaker AS200 (manufactured by Retsch GmbH) and shaken for 30 minutes with a shaking width of 0.3 mm. At this time, the calculated value of the acceleration undergone by the particulate water-absorbing agent is 2.2 G at the maximum. The particulate water-absorbing agent after shaking was designated as a comparative particulate water-absorbing agent (19). The water absorption performance of the comparative particulate water-absorbing agent (19) is shown in Table 3.

Comparative Example 2-6

A comparative particulate water-absorbing agent (20) was obtained by carrying out the same operations as in Comparative Example 2-5 except that the shaking time was changed to 300 minutes. The water absorption performance of the comparative particulate water-absorbing agent (20) is shown in Table 3.

TABLE 2

| | Precursor water-absorbing resin | Additive | Mixing time [min] | CRC [g/g] | AAP 2.06 kPa [g/g] |
|---|---|---|---|---|---|
| Example 2-1 | Precursor water-absorbing resin (E) | (1) | 30 | 35.2 | 30.9 |
| Example 2-2 | Precursor water-absorbing resin (E) | (4) | 60 | 35.1 | 31.8 |
| Example 2-3 | Precursor water-absorbing resin (E) | (3) | 60 | 37.4 | 29.7 |
| Example 2-4 | Precursor water-absorbing resin (E) | Aluminum sulfate aqueous solution | 60 | 34.6 | 30.2 |
| Example 2-5 | Precursor water-absorbing resin (F) | (4) | 60 | 33.1 | 31.6 |
| Example 2-6 | Precursor water-absorbing resin (F) | (3) | 45 | 34.9 | 31.4 |
| Example 2-7 | Precursor water-absorbing resin (F) | Aluminum hydroxide | 60 | 34.3 | 30.3 |
| Example 2-8 | Precursor water-absorbing resin (F) | Aluminum sulfate aqueous solution | 60 | 35.5 | 30.4 |
| Example 2-9 | Precursor water-absorbing resin (E) | (1) | 15 | 35.5 | 30.4 |
| Comparative Example 2-1 | Precursor water-absorbing resin (E) | (1) | 2 | 35.3 | 29.9 |
| Comparative Example 2-2 | Precursor water-absorbing resin (E) | (3) | 2 | 37.2 | 28.6 |
| Comparative Example 2-3 | Precursor water-absorbing resin (F) | (4) | 2 | 32.9 | 30.6 |
| Comparative Example 2-4 | Precursor water-absorbing resin (F) | (3) | 2 | 35.1 | 30.2 |

| | RCAP 2.06 kPa [g/g] | AAP2.06 kPa + RCAP2.06 kPa [g/g] | Evaluation of absorbent body A used for diapers (Absorbent body A) Absorption capacity (g) | Evaluation of absorbent body B used for diapers (Absorbent body B) Absorption capacity (g) |
|---|---|---|---|---|
| Example 2-1 | 46.3 | 77.2 | 144 | 120 |
| Example 2-2 | 45.8 | 77.6 | 144 | 120 |
| Example 2-3 | 47.7 | 77.4 | 146 | 122 |
| Example 2-4 | 47.4 | 77.6 | 145 | 121 |
| Example 2-5 | 45.0 | 76.6 | 142 | 118 |
| Example 2-6 | 45.8 | 77.2 | 143 | 120 |
| Example 2-7 | 47.9 | 78.2 | 146 | 122 |
| Example 2-8 | 48.0 | 78.4 | 146 | 123 |

TABLE 2-continued

| | | | | |
|---|---|---|---|---|
| Example 2-9 | 45.8 | 76.2 | 142 | 118 |
| Comparative Example 2-1 | 45.4 | 75.3 | 139 | 117 |
| Comparative Example 2-2 | 46.6 | 75.2 | 139 | 117 |
| Comparative Example 2-3 | 43.7 | 74.3 | 138 | 114 |
| Comparative Example 2-4 | 45.0 | 75.2 | 140 | 116 |

(Note)
Additive column (1) silicon dioxide (REOLOSIL QS-20),
(3) silicon dioxide (Sipernat 22S),
(4) silicon dioxide (OSC C132)

TABLE 3

| | CRC [g/g] | AAP2.06 kPa [g/g] | RCAP2.06 kPa [g/g] | AAP2.06 kPa + RCAP2.06 kPa [g/g] | Evaluation of absorbent body A used for diapers (Absorbent body A) Absorption capacity (g) | Evaluation of absorbent body B used for diapers (Absorbent body B) Absorption capacity (g) |
|---|---|---|---|---|---|---|
| Comparative Example 2-5 | 32.6 | 28.5 | 44.5 | 73.0 | 137 | 113 |
| Comparative Example 2-6 | 32.5 | 28.8 | 43.4 | 72.2 | 136 | 111 |

As can be seen from the evaluation results of the absorbent bodies in Table 2, each of the particulate water-absorbing agents of the Examples, which is a particulate water-absorbing agent satisfying the expression (1), had a higher liquid retention capacity (absorption capacity) under pressure by 2 g or more even in a state in which the particulate water absorbent absorbed the liquid and swelled, when used as an absorbent body, than those of the Comparative Examples. This difference in the liquid capacity is a remarkable difference in the art. From this result, it can be seen that each of the particulate water-absorbing agents of the Examples can significantly reduce the re-wet even if pressure is applied to the particulate water-absorbing agent from the outside when the particulate water-absorbing agent is in a swollen state.

In each of the Examples, the Gel Permeation Rate (GPR) is 20 g/min or more, the blocking ratio after moisture absorption is 40% by weight or less, the Flow Rate is 8.5 g/s or more, the amount of dust was 400 mg/kg or less, the surface tension was 65 mN/m or more, and the water-absorbing resin powder was in an irregularly crushed form.

The present application is based on Japanese Patent Application No. 2020-064626, filed on Mar. 31, 2020, the disclosure of which is incorporated herein by reference in its entirety.

REFERENCE SIGNS LIST

400: apparatus
410: container
411: cell
412: piston
413*a*,
413*b*: wire mesh
414: Swollen gel (obtained by causing water-absorbed particulate water-absorbing agent to absorb water)
415: hole
420: tank
421: glass tube
422: L-shaped tube equipped with cock glass tube
423: liquid
431: stainless steel wire mesh
432: collection container
433: even balance

The invention claimed is:

1. A particulate water-absorbing agent comprising a surface-crosslinked polyacrylic acid (salt)-based water-absorbing resin as a main component and satisfying the following expression (1):

$$AAP(2.06\,kPa)+RCAP(2.06\,kPa)\geq 0.58\times CRC+55.6 \quad (1)$$

wherein AAP (2.06 kPa) represents absorption capacity (g/g) under a pressure of 2.06 kPa, RCAP (2.06 kPa) represents retention capacity against pressure after swelling (g/g), and CRC represents absorption capacity without pressure (g/g) and wherein the CRC is 30 g/g or more.

2. The particulate water-absorbing agent according to claim 1, satisfying the following expression (A):

$$AAP(2.06\,kPa)+RCAP(2.06\,kPa)>76.0. \quad (A)$$

3. The particulate water-absorbing agent according to claim 1, satisfying the following expression (2):

$$AAP(2.06\,kPa)+RCAP(2.06\,kPa)\geq 0.58\times CRC+56.0. \quad (2)$$

4. The particulate water-absorbing agent according to claim 1, satisfying the following expression (3):

$$AAP(2.06\,kPa)+RCAP(2.06\,kPa)\geq 0.58\times CRC+56.5. \quad (3)$$

5. The particulate water-absorbing agent according to claim 1, wherein AAP (4.83 kPa) (swelling capacity (g/g) under a pressure of 4.83 kPa) is 10 g/g or more.

6. The particulate water-absorbing agent according to claim 1, wherein the AAP (2.06 kPa) (swelling capacity (g/g) under a pressure of 2.06 kPa) is 20 g/g or more.

7. The particulate water-absorbing agent according to claim 1, wherein a Gel Permeation Rate (GPR) is 20 g/min or more.

8. The particulate water-absorbing agent according to claim 1, wherein a blocking ratio after moisture absorption is 40% by weight or less.

9. The particulate water-absorbing agent according to claim 1, wherein a Flow Rate is 8.5 g/s or more.

10. The particulate water-absorbing agent according to claim 1, wherein an amount of dust is 400 mg/kg or less.

11. The particulate water-absorbing agent according to claim 1, wherein a surface tension is 65 mN/m or more.

12. The particulate water-absorbing agent according to claim 1, wherein the water-absorbing resin is in an irregularly crushed form.

13. The particulate water-absorbing agent according to claim 1, further comprising at least one kind selected from the group consisting of a water insoluble inorganic particle and a water soluble polyvalent metal cation-containing compound.

14. An absorbent body comprising the particulate water-absorbing agent according to claim 1.

15. A hygiene article comprising the absorbent body according to claim 14.

* * * * *